US008614254B2

(12) United States Patent
Llinas et al.

(10) Patent No.: US 8,614,254 B2
(45) Date of Patent: Dec. 24, 2013

(54) METHODS AND COMPOSITIONS FOR TREATING THALAMOCORTICAL DYSRHYTHMIA

(75) Inventors: Rodolfo R. Llinas, New York, NY (US); Mutsuyuki Sugimori, New York, NY (US); Francisco Urbano, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/843,108

(22) Filed: Jul. 26, 2010

(65) Prior Publication Data
US 2010/0292344 A1 Nov. 18, 2010

Related U.S. Application Data

(62) Division of application No. 12/045,265, filed on Mar. 10, 2008, now abandoned.

(60) Provisional application No. 60/906,085, filed on Mar. 9, 2007.

(51) Int. Cl.
*A61K 31/045* (2006.01)

(52) U.S. Cl.
USPC .......................................................... 514/724

(58) Field of Classification Search
USPC .......................................................... 514/724
See application file for complete search history.

(56) References Cited

U.S. PATENT DOCUMENTS

| | | | |
|---|---|---|---|
| 4,897,426 A | 1/1990 | Llinas et al. | |
| 6,635,652 B1 | 10/2003 | Kawashima et al. | |
| 6,878,111 B2 | 4/2005 | Kenknight et al. | |
| 2003/0096868 A1 | 5/2003 | Harper et al. | |
| 2003/0108606 A1 | 6/2003 | Norden et al. | |
| 2004/0097598 A1 | 5/2004 | Likhodi et al. | |
| 2007/0117869 A1 | 5/2007 | Epstein et al. | |
| 2007/0212428 A1 | 9/2007 | Wittlin | |
| 2008/0103157 A1 | 5/2008 | Yamaguchi et al. | |

FOREIGN PATENT DOCUMENTS

| | | |
|---|---|---|
| GB | 1242547 A | 8/1971 |
| GB | 2029700 A | 3/1980 |
| WO | 00/21521 A2 | 4/2000 |
| WO | 02/062327 A2 | 8/2002 |
| WO | 2003/055424 A1 | 7/2003 |
| WO | 2006/138048 A2 | 12/2006 |
| WO | 2007/022924 A2 | 3/2007 |
| WO | 2008/095297 A1 | 8/2008 |

OTHER PUBLICATIONS

Bourinet, et al., "Silencing of the Cav3.2 T-Type Calcium Channel Gene in Sensory Neurons Demonstrates its Major Role in Nociception," Embo, J., 24:315-324 (2005).

Catterall, et al., "International Union of Pharmacology. XLVII. Nomenclature and Structure-Function Relationships of Voltage-Gated Calcium Channels," Pharmacol. Rev., 57:411-425 (2005).

Kang, et al., "A Molecular Determinant of Nickel Inhibition in Cav3.2T-Type Calcium Channels," J. Biol. Chem., 281 (8):4823-4830 (2006).

Khosravani, et al., "Gating Effects of Mutations in the Cav3.2T-Type Calcium Channels Associated With Childhood Absence Epilepsy," J. Biol. Chem., 279(11):9681-9684 (2004).

Khosravani, et al., "Effects of Cav3.2 Channel Mutations Linked to Idiopathic Generalized Epilepsy," Ann. Neurol., 57(5):745-749 (2005).

Michels, et al., "Single-Channel Pharmacology of Mibefradil in Human Native T-Type and Recombinant Cav3.2 Calcium Channels," Mol. Pharmacol., 61(3):682-694 (2002).

Murbartian, et al., "Alternative Splicing of the Rate Cav3.3 T-Type Calcium Channel Gene Produces Variants With Distinct Functional Properties," FEBS Letters, 528:272-278 (2002).

Peloquin, et al., "Functional Analysis of Cav3.2 T-Type Calcium Channel Mutations Linked to Childhood Absence Epilepsy," Epilepsia, 47(3):655-658 (2006).

Yunker, et al., "Immunological Characterization of T-Type Voltage-Dependent Calcium Channel Cav3.1 (Alpha1G) and Cav3.3 (Alpha1I) Isoforms Reveal Differences in Their Localization, Expression, and Neural Development," Neuroscience 117:321-335 (2003).

Yunker, et al., "Corrigendum to: Immunological Characterization of T-Type Voltage-Dependent Calcium Channel Cav3.1 (Alpha1G) and Cav3.3 (Alpha1I) Isoforms Reveal Differences in Their Localization, Expression, and Neural Development," Neuroscience 142:607 (2006).

Coulter, et al., "Differential effects of petit mal anticonvulsants and convulsants on thalamic neurones: calcium current reduction," Br. J. Pharmacol. (1990) 100:800-806.

Cribbs, et al., "Identification of the T-Type Calcium Channel (CaV3.1d) in Developing Mouse Heart," Cir. Res. (2001) 88:403-407.

Degterev, et al., "Identification of small-molecule inhibitors of interaction between the BH3 domain and Bcl-xL," Nat. Cell Biol. (2001) 3:173-182.

Freeze, et al., "State-dependent verapamil block of the cloned human CaV3.1 T-type Ca2+ channel," Mol. Pharmacol. (2006).

Ertel, et al., "Nomenclature of Voltage-Gated Calcium Channels," Neuron (2000) 25:533-535.

(Continued)

*Primary Examiner* — Paul Zarek
(74) *Attorney, Agent, or Firm* — Ann-Louise Kerner; K&L Gates LLP

(57) ABSTRACT

This invention relates to methods of inhibiting a $Ca_v3$ calcium channel in a cell using a $C_2$-$C_{10}$ alkyl alcohol, or mixtures thereof. This invention further relates to methods of treating a thalamocortical dysrhythmia disorder in a mammal and for treating a neurological disorder in a mammal associated with the thalamocortical dysrhythmia using a $C_2$-$C_{10}$ alkyl alcohol, a lipophilic molecule with a partition coefficient substantially similar to that of a $C_2$-$C_{10}$ alkyl alcohol, or mixtures thereof, or a pharmaceutical composition comprising the same.

15 Claims, 8 Drawing Sheets

(56) References Cited

OTHER PUBLICATIONS

Gruneberg, et al., "Successful Virtual Screening for Novel Inhibitors of Human Carbonic Anhydrase: Strategy and Experimental Confirmation," J. Med. Chem. (2002) 45:3588-3602.

Hideto, et al., "Differential Expression of c-Fos Following Administration of Two Tumerogenic Agents: Harmaline and Oxotremorine," NeuroReport (2000) 11:2385-2390.

Jahnsen, et al., "Electrophysiological Properties of Guinea-Pig Thalamic Neurones: An In Vitro Study," J. Physiol. (1984) 349:205-226.

Jeanmonod, et al., "Low-threshold calcium spike bursts in the human thalamus Common physiopathology for sensory, motor and limbic positive systems," Brain (1996) 119:363-375.

Jeanmonod, et al., "Surgical control of the human thalamocortical dysrhythmia: I. Central lateral thalamotomy in neurogenic pain," Thalamus & Related Systems (2001) 1:71-79.

Jeanmonod, et al., "Neuropsychiatric thalamocortical dysrhythmia: surgical implications," Thalamus & Related Systems (2003) 2:103-113.

Jiang, et al., X-ray structure of a voltage-dependent K+ channel, Nature (2003) 423:33-41.

Jones, "Calcium channels in higher-level brain function," Proc. Natl Acad. Sci. USA (2007) 104(46):17903-17904.

Jun, et al., "Ablation of P/Q-type Ca2+ channel currents, altered synaptic transmission, and progressive ataxia in mice lacking the α1A- subunit," Proc. Natl. Acad. Sci. U S A (1999) 96(26):15245-15250.

Kim, et al., "Lack of the Burst Firing of Thalamocortical Relay Neurons and Resistance to Absence Seizures in Mice Lacking α1G T-Type Ca2+ Channels," Neuron (2001) 31:35-45.

Llinas, et al., "Electrophysiology of mammalian thalamic neurones in vitro," Nature (1982) 297:406-408.

Llinas, et al., "Thalamocortical dysrhythmia: A neurological and neuropsychiatric syndrome characterized by magnetoencephalography," Proc. Natl. Acad. Sci. U S A. (1999) 96(26):15222-15227.

Llinas, et al., "Rhythmic and dysrhythmic thalamocortical dynamics: GABA systems and the edge effect," Trends Neurosci. (2005) 28(6):325-333.

Llinas, et al. "Bursting of Thalamic Neurons and States of Vigilance," J. Neurophysiol. (2006) 95:3297-3308.

Llinas, et al., "γ-Band deficiency and abnormal thalamocortical activity in P/Q-type channel mutant mice," Proc. Natl. Acad. Sci. U S A (2007) (104)45:17819-17824.

Long, et al., "Crystal Structure of a Mammalian Voltage-Dependent Shaker Family K+ Channel," Science (2005) 309:897-903.

Mckay, et al., "Ca(v)3 T-type calcium channel isoforms differentially distribute to somatic and dendritic compartments in rat central neurons," Eur. J. Neurosci. (2006) 24(9):2581-2594.

McGrath, "Causes of Asperger's Syndrome: Reality and Myths About Autism Spectrum Disorders," www.suite101.com (Jun. 15, 2008).

Meir, "T-type Cav channels," Modulator (2003) 17:1-3.

Moran, et al., "Parkinson's disease: Thalamocortical dysrhythmia," Soc. Neurosci. Abst. (2004) 676.12.

Pedroarena, et al., "Dendritic calcium conductances generate high-frequency oscillation in thalamocortical neurons," Proc. Natl. Acad. Sci. U S A (1997) 94:724-728.

Perez-Reyes, "Molecular Physiology of Low-Voltage-Activated T-type Calcium Channels," Physiol. Rev. (2003) 83:117-161.

Schapira, et al., "Rational discovery of novel nuclear hormone receptor antagonists," Proc. Natl. Acad. Sci. USA (2000) 97(3):1008-1013.

Schapira, et al., "Discovery of diverse thyroid hormone receptor antagonists by high-throughput docking," Proc. Natl. Acad. Sci. USA (2003) 100(12):7354-7359.

Schulman, et al., "Thalamocortical Dysrhythmia in Depression and Obsessive-Compulsive Disorder," Soc. Neurosci. Abst. (2001) 27:111.4.

Schulman, et al., "Thalamocortical dysrhythmia syndrome: MEG imaging of neuropathic pain," Thalamus & Related Systems (2005) 3(1): 33-39.

Schwartzman, et al., "Neuropathic Central Pain: Epidemiology, Etiology, and Treatment Options," Arch. Neurol. (2001) 58:1547-1550.

Sinton, et al., "The effectiveness of different isomers of octanol as blockers of harmaline-induced tremor," Pflügers Archiv. J. Phys. (1989) 414:31-36.

Song, et al., "Role of T-type calcium channels in the genesis of absence seizure in the mutant mice for α1A, the pore-forming subunit of the P/Q-type calcium channel," Soc. Neurosci. Abstr. (2001) 151.21.

Volkmann, et al., "Central motor loop oscillations in parkinsonian resting tremor revealed by magnetoencephalography," Neurol. (1996) 46(5):1359-1370.

Wang, et al., "Targeting Bcl-2 and Bcl-XL With Nonpeptidic Small-Molecule Antagonists," Semin. Oncol. (2003) 30 (5):133-142.

White, et al., "Transient low-threshold Ca2+ current triggers burst firing through an afterdepolarizing potential in an adult mammalian neuron," Proc. Natl. Acad. Sci. USA (1989) 86:6802-6806.

Wikipedia, "Verapamil", 2010.

Wikipedia, "Pimozide", 2010.

Bal et al. (1997) "Synchronized Oscillations in the Inferior Olive Are Controlled by the Hyperpolarization-Activated Cation Current Ih," J. Neurophysiol. 77:3145-3156.

Fransén et al. (2004) "Ionic Mechanisms in the Generation of Subthreshold Oscillations and Action Potential Clustering in Entorhinal Layer II Stellate Neurons," Hippocampus 14:368-384.

Talley et al. (1999) "Differential Distribution of There Members of a Gene Family Encoding Low Voltage-Activated (T-? Type) Calcium Channels," J. Neurosci. 19(6):1895-1911.

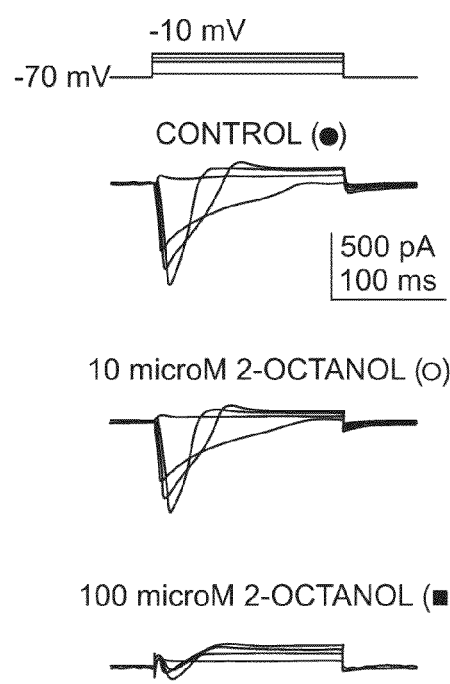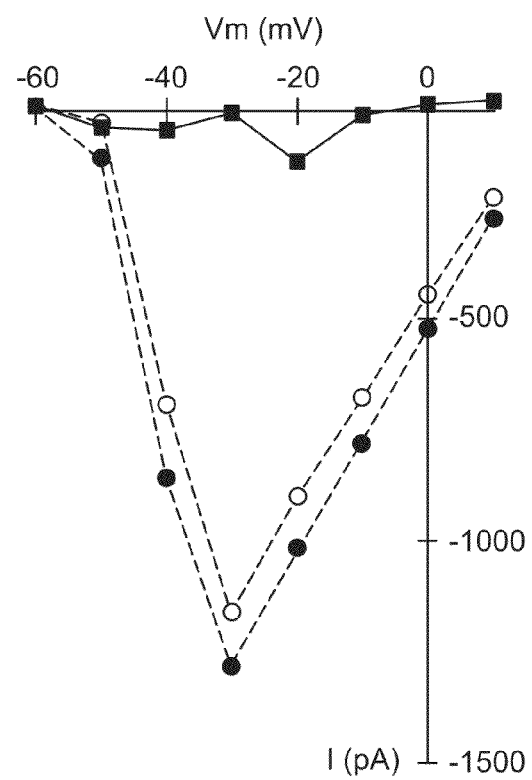
FIG. 2A
FIG. 2B

METHODS AND COMPOSITIONS FOR TREATING THALAMOCORTICAL DYSRHYTHMIA

CROSS REFERENCE TO RELATED APPLICATIONS

This application is a division of U.S. patent application Ser. No. 12/045,265 filed Mar. 10, 2008, which claims the benefit of priority under 35 U.S.C. §119(e) to U.S. Provisional Patent Application No. 60/906,085 filed on Mar. 9, 2007, each of the aforementioned applications is hereby incorporated by reference in its entirety.

FIELD OF THE INVENTION

This invention relates to the medical sciences generally and neurophysiology and neuropharmacology in particular. More specifically, this invention relates to methods and compositions for treating a neurological disorder in a mammal and for an associated thalamocortical dysrhythmia using a $C_2$-$C_{10}$ alkyl alcohol, or a lipophilic molecule with a partition coefficient substantially similar to that of a $C_2$-$C_{10}$ alkyl alcohol, or mixtures thereof.

BACKGROUND OF THE INVENTION

Neurological disorders that affect the central nervous system, the peripheral nervous system, and the autonomic nervous system strick millions of people worldwide. These varied disorders include, but are not limited to, thalamocortical dysrhythma, neurogenic pain, obsessive-compulsive disorder, depression, panic disorder, Parkinson's disease, schizophrenia, rigidity, dystonia, tinnitus, tremor, and epilepsy. In particular, these and other neurological disorders occur when the coordinate, controlled electrical activity at the cortical level of the brain becomes disrupted, thereby leading to uncoordinated electrical activity and abnormal neuronal oscillation.

In particular, thalamocortical dysrhythmia refers to a neurological and/or psychiatric condition arising from the abnormal rhythmicity in particular components of the thalamocortical circuit Winds et al. (1999) *Proc. Natl. Acad. Sci. USA*, 96:15222-15227). At the cellular level, the abnormal activity of the thalamic neurons is caused by an increase of low frequency oscillatory activity due to protracted activation of the T type calcium channels because of direct modification of the channel properties or more commonly, abnormal hyperpolarization of the thalamic neurons due to excess inhibition or deafferentation. Such abnormal activity is transmitted to the related cortical area to which the given thalamic neurons are oscillating generating a recurrent attractor that is maintained by the recursive nature of the circuit. At the macrocellular level, the abnormal rhythmicity interferes with the communication among and between different regions of the brain, and thereby impairs the motor and cognitive skills that are controlled by those regions of the cortex.

Spike output in neuronal cell types is affected by low-voltage-activated Cav3-type calcium currents arising from the $Ca_v$ channels. Low-voltage-activated (LVA) calcium currents provide an important contribution to spike output patterns of neurons. Cav3-type channels are recognized as key determinants of LVA calcium-dependent responses, including low-threshold calcium spikes (LTS), bistable behavior, rebound depolarizations and augmentation of synaptic responses. Cav3-type channels are important to cell and circuit functions that range from sensory and pain transmission through thalamocortical sleep-wake cycles. The three isoforms of the Cav3-type calcium channel, i.e., $Ca_v3.1$, $Ca_v3.2$, and $Ca_v3.3$, can differ in their voltage-dependent and kinetic properties, demonstrating the potential to differentially affect spike output. In thalamus, differences in the distribution and kinetic properties of Cav3-type currents have been shown to be capable of influencing the nature of oscillatory output of principal cells and inhibitory interneurons involved in the sleep-wake cycle, suggesting a selective distribution or modulation of $Ca_v3$ channel isoforms over discrete regions of the cell axis.

There are many drugs currently available for treating neurological disorders. These include, but are not limited to, anticonvulsants, antiepileptics, barbiturates, barbituric acid derivatives, anesthetic agents, tinnitus-treating agents, selective serotonin reuptake inhibitors, antidepressant agents, neuroleptic agents, antihypertensive agents, antipsychotic agents, calcium channel blockers, ACE inhibitors, and beta-blockers. However, many of such drugs are limited in their effectiveness and by their significant side effects. For example, some of these drugs are known to cause lightheadedness, depression insomnia, weakness, fatigue, hallucinations, side-effects which severely limit their use in human population. In particular, beta blockers, anticonvulsants, and benzodiazepines have been shown to be partially beneficial to some patients. However, beta blockers can cause changes in blood pressure and heart rate, and are contraindicated in patients with heart block, asthma, and congestive heart failure.

In addition, some anticonvulsants can cause acute nausea and vomiting, fatigue, sleepiness, confusion and incoordination, while others can cause memory and speech abnormalities, sedation, incoordination, and metabolic dysfunction.

Physical trauma has been used to treat some neurological disorders. For example, certain surgical procedures have been used in the most severe cases of essential tremor, destroying a part of the brain including, the globus pallidus pars interna (GPi) nucleus in the basal ganglia or implanting electrodes into the same area of the brain including connecting them to a pacemaker-like battery that stimulates regions of the brain to diminish the tremor. Such procedures carry a high risk of infection and bleeding or equipment malfunction. Additionally, many existing treatments for some neurological disorders are poorly effective in that they do not stop the disorders completely, and in most instances, they do not prevent or even delay the progression of the disease.

Thus, there is a need for more effective treatments of neurological disorders that have reduced or no side-effects.

SUMMARY OF THE INVENTION

It has been determined that certain alkyl alcohols, or mixtures thereof, can modify the voltage-dependent activation kinetics or single channel ionic conductance of a $Ca_v3$ calcium channel in a mammalian cell. This finding has been exploited to develop the present invention, which is directed to methods of treating neurological disorders in a mammal associated with thalamocortical dysrhythmia.

In one aspect, the invention relates to a method of reducing a low-threshold-activated calcium current in a cell by having a $Ca_v3$ plasmalemmal-bound calcium channel. The method comprises superfusing the extracellular environment of the cell with a $C_2$-$C_{10}$ alkyl alcohol, or mixtures thereof, in an amount sufficient to modify the voltage-dependent activation kinetics or single channel ionic conductance of the $Ca_v3$ calcium channel such that the low-threshold-activated calcium current in the cell is reduced. In some other embodiments, the $C_2$-$C_{10}$ alkyl alcohol is present in the extracellular environment at a concentration of from about 10 µM to about 100 µM. In certain embodiments, the cell is in a mammal in need of inhibiting a $Ca_v3$ calcium channel.

In some other embodiments, the cell is a neuron, such as an interneuron, a projection thalamic neuron, a reticular thalamic neuron, a cortical interneuron, cortical pyramidal neuron, a basal ganglion neuron, a hippocampus neuron, an amygdala neuron, a tectal neuron, or a cerebellar neuron. In particular embodiments, the $Ca_v3$ calcium channel is selected from the group consisting of a $Ca_v3.1$ calcium channel, a $Ca_v3.2$ calcium channel, a $Ca_v3.3$ calcium channel, and combinations thereof. In certain embodiments, the $C_2$-$C_{10}$ alkyl alcohol is administered in a pharmaceutically acceptable excipient, carrier, or diluent.

In another aspect, the invention relates to a method of inhibiting a $Ca_v3$ plasmalemmal-bound calcium channel in a cell of a mammal in need thereof. The method comprises administering to the mammal a $C_2$-$C_{10}$ alkyl alcohol, or mixtures thereof, at a dose of from about 0.001 mg/kg body weight to about 20 mg/kg body weight of the mammal, for example, from about 0.01 mg/kg to about 1 mg/kg, from about 0.1 mg/kg to about 10 mg/kg, from about 0.3 mg/kg to about 3 mg/kg. The alcohol modifies the voltage-dependent activation kinetics or single channels ionic conductance of the $Ca_v3$ calcium channel, thereby inhibiting the $Ca_v3$ calcium channel. In one embodiment, the alcohol is administered orally. In another embodiment, the alcohol is administered parenterally. In particular embodiments, the $C_2$-$C_{10}$ alkyl alcohol is 1-octanol or 2-octanol. In a further embodiment, the mammal has a thalamocortical dysrhythmia disorder, and in another embodiment, the mammal is a human.

The invention also provides a method of treating a thalamocortical dysrhythmia disorder that is not tremor or Parkinson's tremor in a mammal in need thereof. The method comprises administrating to the mammal a therapeutically effective amount of a $Ca_v3$ calcium channel inhibitor which binds to the $Ca_v3$ calcium channel, thereby reducing a low voltage-activated calcium current in the cell of the mammal. In one embodiment, the mammal is a human. In some embodiments, the inhibitor is a $C_2$-$C_{10}$ alkyl alcohol, or mixtures thereof.

In a further aspect, the invention provides a method of treating a neurological disorder in a mammal in need thereof provided that the neurological disorder is not tremor or Parkinson's tremor. The method comprises administering to the mammal a therapeutically effective amount of a $Ca_v3$ calcium channel inhibitor. In certain embodiments, the $Ca_v3$ calcium channel inhibitor is a $C_2$-$C_{10}$ alkyl alcohol, or mixtures thereof. In other embodiments, the $Ca_v3$ calcium channel inhibitor is a lipophilic molecule with a partition coefficient substantially similar to that of a $C_2$-$C_{10}$ alkyl alcohol. In a particular embodiment, the $Ca_v3$ calcium channel inhibitor is a lipophilic molecule with a partition coefficient substantially similar to that of an octanol. In another embodiment, the $Ca_v3$ calcium channel inhibitor is a lipophilic molecule with a molecular weight less than about 160.

In one embodiment, the neurological disorder is a thalamocortical dysrhythmia disorder. In some embodiments, the thalamocortical dysrhythmia disorder being treated is petit mal epilepsy, tinnitus, neurogenic pain, Tourettes disease, chronic depression, autism or Asperger's syndrome, schizoaffective psychosis, Parkinson's disorder, Migraine, Absence Epilepsy, or restless legs syndrome.

In certain embodiments, the therapeutically effective amount of $Ca_v3$ calcium channel inhibitor administered is from about 0.001 mg/kg body weight to about 20 mg/kg body weight of the mammal, from about 0.01 mg/kg body weight to about 1 mg/kg body weight of the mammal, from about 0.1 mg/kg body weight to about 10 mg/kg body weight of the mammal, from about 0.03 mg/kg body weight to about 0.3 mg/kg body weight of the mammal, from about 0.3 mg/kg body weight to about 3.0 mg/kg body weight of the mammal, or about 1.0 mg/kg body weight of the mammal.

In certain embodiments, the $C_2$-$C_{10}$ alkyl alcohol is selected from the group consisting of (a) $CH_3$—$(CH_2)_n$—OH, wherein n is an integer from 1 to 9, (b) $CH_3$—$CH(OH)$—$(CH_2)_m$—$CH_3$, wherein m is an integer from 0 to 7, (c) $CH_3$—$CH_2$—$CH(OH)$—$(CH_2)_p$—$CH_3$, wherein p is an integer from 0 to 6, (d) $CH_3$—$CH_2$—$CH_2$—$CH(OH)$—$(CH_2)_q$—$CH_3$, wherein q is an integer from 0 to 5, (e) $CH_3$—$CH_2$—$CH_2$—$CH_2$—$CH(OH)$—$(CH_2)_w$—$CH_3$, wherein w is an integer from 0 to 4, and (f) mixtures thereof.

The invention also provides a use of a $Ca_v3$ calcium channel inhibitor which binds to the $Ca_v3$ calcium channel, thereby reducing a low voltage-activated calcium current in the cell of the mammal, in the manufacture of a medicament for the treatment of a neurological disorder in a mammal, provided that the neurological disorder is not tremor or Parkinson's tremor.

The invention further provides a use of a $Ca_v3$ calcium channel inhibitor which binds to the $Ca_v3$ calcium channel, thereby reducing a low voltage-activated calcium current in the cell of the mammal, in the manufacture of a medicament for the treatment of a thalamocortical dysrhythmia disorder in a mammal, provided that the thalamocortical dysrhythmia disorder is not tremor or Parkinson's tremor.

The invention also provides a method for identifying an alkyl alcohol that modifies the voltage-dependent activation kinetics or single channel ionic conductance of a $Ca_v3$ plasmalemmal-bound calcium channel protein. The method comprises (a) providing atomic coordinates of the $Ca_v3$ calcium channel protein; (b) subjecting an alkyl alcohol to computational molecular docking; and (c) selecting the alcohol that has the optimal virtual binding to the a $Ca_v3$ calcium channel protein. Optimal virtual binding indicates that the alcohol binds to the a $Ca_v3$ calcium channel protein or alters the properties of the lipid bilayer at the channel's voltage sensing site. In certain embodiments, the optimal virtual binding is substantially similar to that as shown in FIG. 8. In some embodiments, the computational molecular docking utilizes a computer screening method selected from the group consisting of Virtual library screening (VLS), ICM, ICM-VLS, DOCK, and FlexX.

In another aspect, the invention provides a method of identifying a chemical entity which binds to a $Ca_v3$ calcium channel. The method comprises comparing a structure model of the $Ca_v3$ calcium channel with a structure model for the chemical entity, and detecting (i) a binding surface on the $Ca_v3$ calcium channel for the chemical entity, or (ii) an alteration of the properties of the lipid bi-layer at the channel's voltage sensing site for the chemical entity. In certain embodiments, the structural model of the $Ca_v3$ calcium channel is derived from a structure-predicting algorithm. In some other embodiments, the $Ca_v3$ calcium channel is selected from the group consisting of a $Ca_v3.1$ calcium channel, a $Ca_v3.2$ calcium channel, a $Ca_v3.3$ calcium channel, and combinations thereof. In certain embodiments, the structure model of the $Ca_v3$ calcium channel is derived from atomic coordinates determined by subjecting a crystal comprising a $Ca_v3$ calcium channel to X-ray diffraction measurements.

In yet another aspect, the invention provides a method of identifying an inhibitor of a $Ca_v3$ calcium channel in a cell. The method comprises contacting an isolated $Ca_v3$ plasmalemmal-bound calcium channel with a candidate compound, and detecting the presence of a complex, or lack thereof, between the $Ca_v3$ calcium channel and the compound. The candidate compound is an inhibitor if it forms a complex with the $Ca_v3$ calcium channel or alters the properties of the lipid bilayer at the channel's voltage sensing site.

In a further aspect, the invention provides a pharmaceutical composition comprising: a therapeutically effective amount of a $C_2$-$C_{10}$ alkyl alcohol, a lipophilic molecule with a partition coefficient substantially similar to that of a $C_2$-$C_{10}$ alkyl alcohol, or mixtures thereof and at least one other therapeutic agent.

In certain embodiments, the $Ca_v3$ calcium channel inhibitor is a $C_2$-$C_{10}$ alkyl alcohol, or mixtures thereof. In some embodiments, the $C_2$-$C_{10}$ alkyl alcohol is 1-octanol or 2-octanol. In other embodiments, the $Ca_v3$ calcium channel inhibitor is a lipophilic molecule with a partition coefficient substantially similar to that of a $C_2$-$C_{10}$ alkyl alcohol. In a particular embodiment, the $Ca_v3$ calcium channel inhibitor is a lipophilic molecule with a partition coefficient substantially similar to that of an octanol. In another embodiment, the $Ca_v3$ calcium channel inhibitor is a lipophilic molecule with a molecular weight less than about 160.

In certain embodiments, the at least one other therapeutic agent is selected from the group consisting of an anticonvulsant or antiepileptic agent, a barbiturate or barbituric acid derivative, an anesthetic agent, a tinnitus-treating agent, a selective serotonin reuptake inhibitor, an antidepressant agent, a neuroleptic agent, an antihypertensive agent, an antipsychotic agent, a calcium channel blocker, an ACE inhibitor, a beta-blocker, and combinations thereof.

In yet another aspect, the invention provides a pharmaceutical composition comprising: a therapeutically effective amount of a $C_2$-$C_{10}$ alkyl alcohol, or mixtures thereof and at least one other therapeutic agent selected from the group consisting of: a barbiturate or barbituric acid derivative, an anesthetic agent, a tinnitus treating agent, a selective serotonin reuptake inhibitor, an antidepressant agent, a neuroleptic, an antihypertensive agent, a calcium channel blocker, and an ACE inhibitor.

In certain embodiments, the anticonvulsant or antiepileptic agent is selected from the group consisting of carbamazepine, clobazam, clonazepam, ethosuximide, felbamate, fosphenyloin, flurazepam, gabapentin, gabapentin, lamotrigine, levetiracetam, oxcarbazepine, mephenyloin, phenobarbital, phenyloin, pregabalin, primidone, sodium valproate, tiagabine, topiramate, valproate semisodium, valproic acid, and vigabatrin, diazepam, lorazepam, paraldehyde, pentobarbital, amiloride, α-methyl-α-phenylsuccinimide, pentylenetetrazole and tert-butyl-bicyclo[2.2.2]phosphorothionate.

In certain other embodiments, the barbiturate or barbituric acid derivative is selected from the group consisting of sodium thiopental, pentobarbital, secobarbital, amobarbital, butabarbital, barbital, phenobarbital, butalbital, cyclobarbital, allobarbital, methylphenobarbital, secobarbital, vinylbital and methohexital. In certain embodiments, the anesthetic agent is selected from the group consisting of propofol, etomidate, isoflurane, halothane, and ketamine. In certain other embodiments, the tinnitus-treating agent is selected from the group consisting of botulinum toxin, propranolol, clonazepam, zinc supplementation, acamprosate, etidronate or sodium fluoride, lignocaine, carbemazepine, melatonin, sertraline and vitamin combinations. In certain embodiments, the selective serotonin reuptake inhibitor is selected from the group consisting of paroxetine, sertraline, fluoxetine and fluvoxamine.

In some embodiments, the antidepressant agent is selected from the group consisting of Harmaline, Iproniazid, Isocarboxazid, Moclobemide, Nialamide, Pargyline, Phenelzine, Selegiline, Toloxatone, Tranylcypromine, Brofaromine, Moclobemide, Amineptine, Phenmetrazine, Vanoxerine, Bupropion, Atomoxetine, Maprotiline, Reboxetine, Viloxazine, Duloxetine, Milnacipran, Nefazodone Venlafaxine, Alaproclate, Citalopram, Escitalopram, Etoperidone, Fluoxetine, Fluvoxamine, Paroxetine, Sertraline, Zimelidine, Tianeptine, Amitriptyline, Amoxapine, Butriptyline, Clomipramine, Desipramine, Dibenzepin, Dothiepin, Doxepin, Imipramine, Iprindole, Lofepramine, Melitracen, Nortriptyline, Opipramol, Protriptyline, Trimipramine, Maprotiline, Mianserin, Nefazodone, and Trazodone.

In certain embodiments, the neuroleptic agent is selected from the group consisting of risperidone, ziprasidone, haloperidol, pimozide and fluphenazine. In certain other embodiments, the antihypertensive agent is selected from the group consisting of clonidine and guanfacine. In certain embodiments, the antipsychotic agent is selected from the group consisting of clozapine, risperidone, olanzapine, quetiapine, ziprasidone, aripiprazole, and amisulpride, valproate semisodium or divalproex sodium, lithium salts, risperidone, quetiapine and atomoxetine. In certain embodiments, the calcium channel blocker is selected from the group consisting of amlodipine, felodipine, nicardipine, nifedipine, nimodipine, nisoldipine, nitrendipine, lacidipine, lercanidipine, verapamil, gallopamil, diltiazem, mibefradil, and menthol. In certain other embodiments, the ACE inhibitor is selected from the group consisting of enalapril, ramipril, quinapril, perindopril, lisinopril, benazepril and fosinopril. In particular embodiments, the beta-blocker is selected from the group consisting of dichloroisoprenaline, practolol, pronethaolol, alprenolol, carteolol, levobunolol, mepindolol, metipranolol, nadolol, oxprenolol, penbutolol, pindolol, propranolol, sotalol, timolol, acebutolol atenolol, betaxolol, bisoprolol, esmolol, metoprolol, nebivolol, carvedilol, celiprolol, labetalol and butoxamine.

In another aspect, the invention provides a method of treating a neurological disorder in a mammal in need thereof, comprises administering to the mammal a therapeutically effective amount of the pharmaceutical composition described hereinabove.

The invention also provides a method of treating a thalamocortical dysrhythmia disorder in a mammal in need thereof, comprises administrating to the mammal a therapeutically effective amount of the pharmaceutical composition described hereinabove.

BRIEF DESCRIPTIONS OF THE DRAWINGS

The foregoing and other objects of the present invention, the various features thereof, as well as the invention itself may be more fully understood from the following description, when read together with the accompanying drawings in which:

FIG. 2A is a schematic representation of recording from an experiment showing the effect of 2-octanol on $Ca_v3$ calcium current at different voltage levels using a voltage clamp technique.

FIG. 2B a schematic representation of recording of an experiment showing the effect of 2-octanol on the current-voltage (i.e., I-V curve) relationship for the same thalamic neuron as described in FIG. 2A, but for a wider range of holding potentials.

Figure 3A:
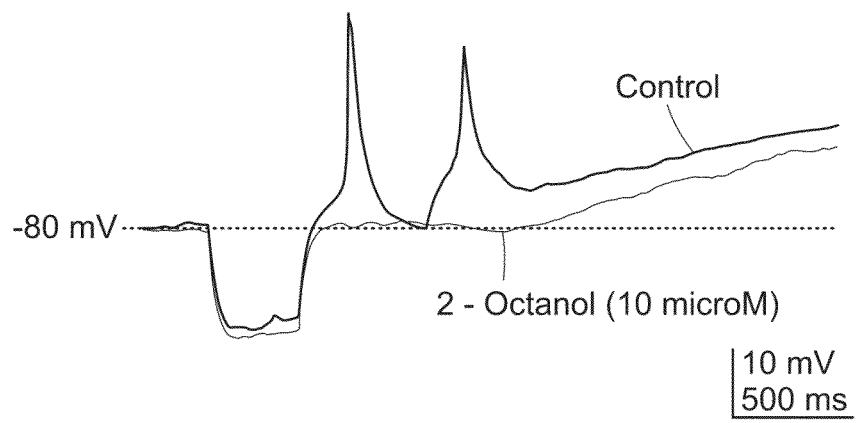

FIG. 3A is a schematic representation of recording from an experiment showing the effect of 1-octanol on thalamic low frequency oscillations using a current clamp technique (a pair of low threshold spikes firing at 2 Hz generated after the rebound of a short hyperpolarizing pulse is applied).

Figure 3B:

FIG. 3B is a schematic representation of recording from an experiment showing the corresponding rebound of a short hyperpolarizing pulse that is applied in FIG. 3A.

Figure 4A:
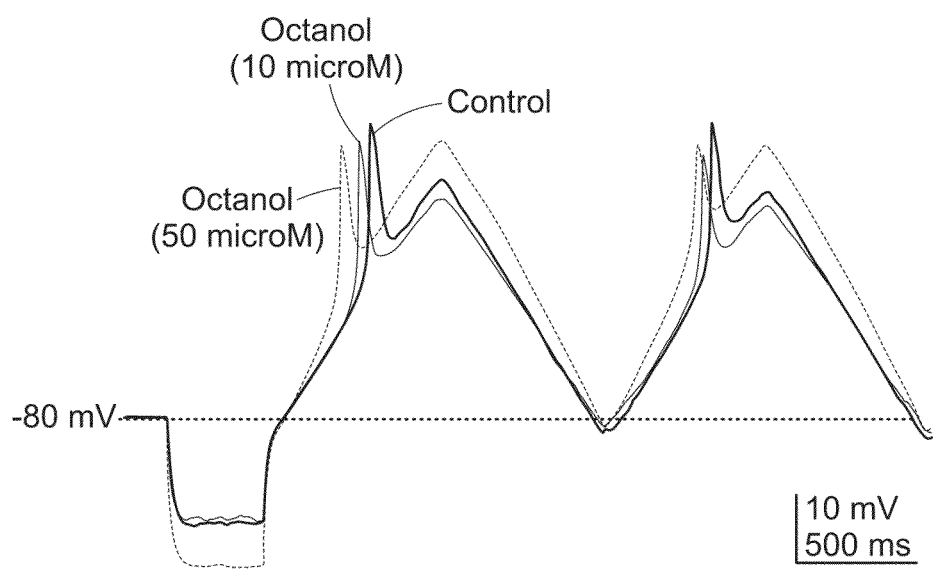

FIG. 4A is a schematic representation of recording from an experiment showing the effect of 1-octanol on low-threshold calcium current using a current clamp technique.

Figure 4B:

FIG. 4B is a schematic representation of recording from an experiment showing the corresponding ramps of current that is applied in FIG. 4A.

Figure 5A:
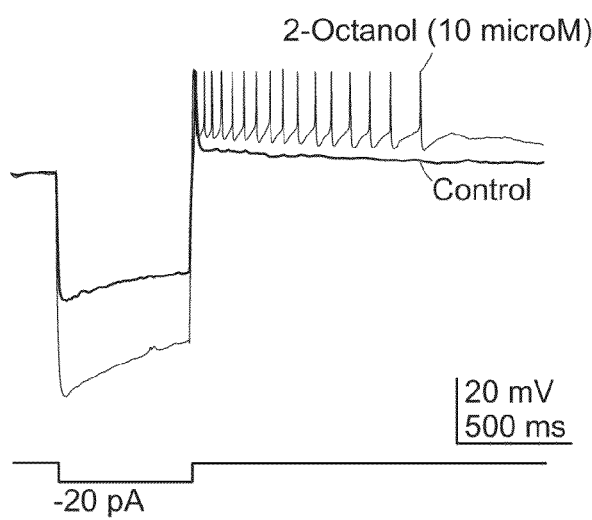

FIG. 5A is a schematic representation of a recording from an experiment showing that low threshold spikes can be activated following TTX removal from the external solution using a current clamp technique.

Figure 5B:
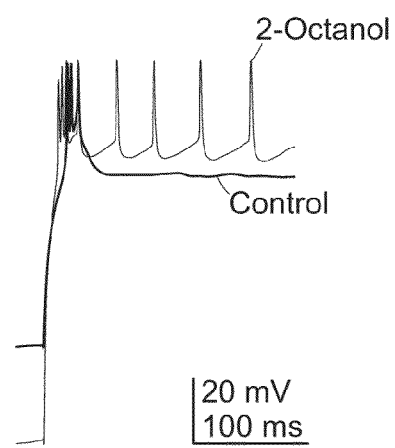

FIG. 5B is a schematic representation of more detailed recording from an experiment showing that low threshold spikes can be activated following TTX removal from the external solution using a current clamp technique.

Figures 6A, 6B:
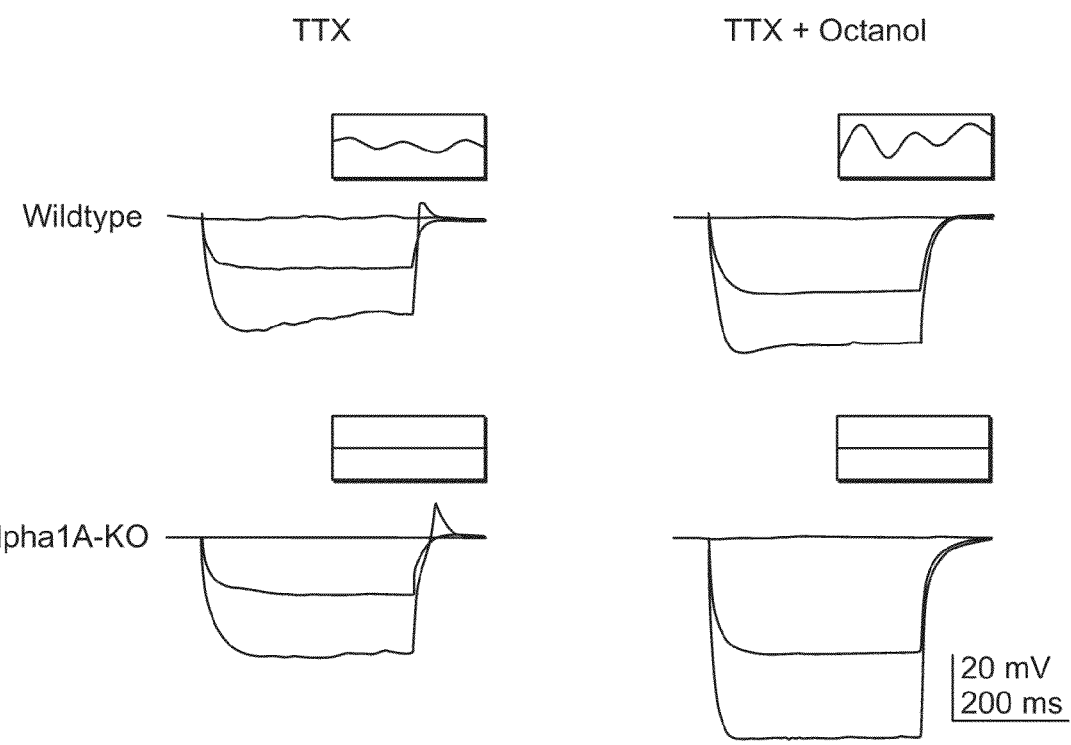

FIG. 6A are schematic representations of recordings from an experiment showing the effect of tetrodotoxin ("TTX") on low-threshold calcium current using a current clamp technique, in both wild type (top) and alpha1A-KO calcium channel knockout (bottom) mice.

FIG. 6B are schematic representations of recordings from an experiment showing the effect of TTX plus 1-octanol on low-threshold calcium current using a current clamp technique, in both wild type (top) and alpha1A-KO calcium channel knockout (bottom) mice.

Figure 7A:
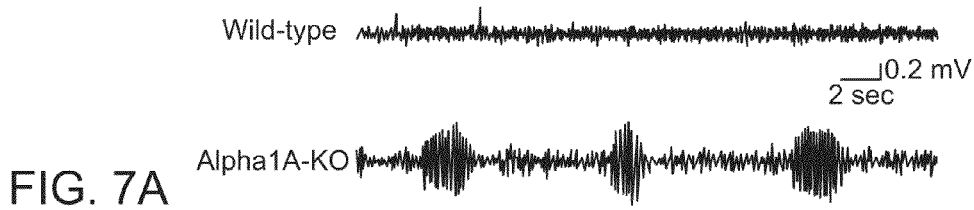

FIG. 7A is a graphic representation of an experiment showing the normal frequency profiles presented in wild type mice.

Figure 7B:
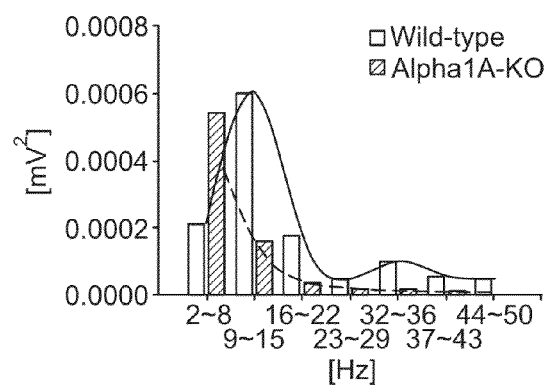

FIG. 7B is a graphic representation of an experiment showing the normal frequency profiles presented in alpha-1A knockout mice.

Figure 7C:
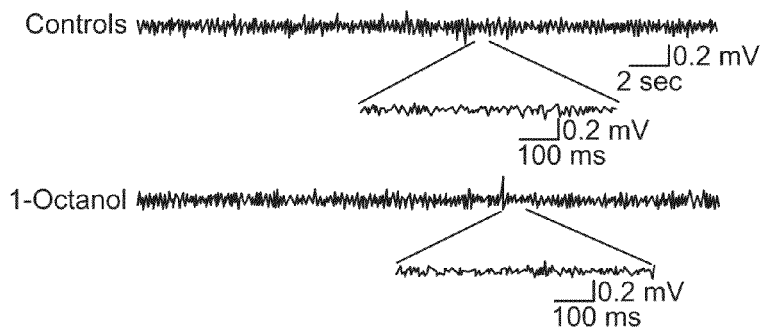

FIG. 7C is a graphic representation of an experiment comparing the frequency profiles presented in both wild-type and alpha1A-knockout mice.

Figure 7D:
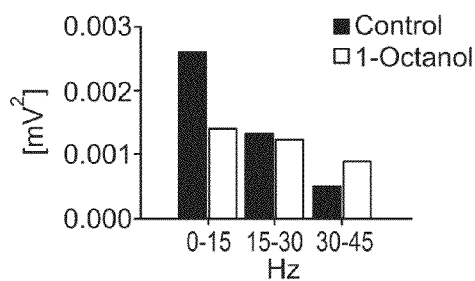

FIG. 7D is a graphic representation of an experiment describing the effect of a 1-octanol injection on the frequency profiles presented in wild-type mice.

Figure 8:

FIG. 8 is a schematic representation of a three-dimension molecular model of a specific binding between 1-octanol and the subunit of a $Ca_v3$ calcium channel shown in one low energy conformation.

DETAILED DESCRIPTION OF THE INVENTION

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

The major theoretical framework of motor and cognitive functions hypothesizes that motor and cognitive functions arise from coordinate electrical activity at the cortical level of the brain. Coordinate electrical activity refers to controlled electrical discharges within the brain at both cellular and macrocellular levels. Controlled electrical discharges facilitate communication within and among different regions of the outer layer of the brain (i.e., the cortex), and thereby coordinate the brain's ability to give rise to both motor and cognitive functions.

At the cellular level, neurons within the brain interact and communicate through electrical signals that are sent between neurons. Neurons transmit electrical signals via an electrochemical process, whereby an exchange of ions occurs across the neuron's membrane, thereby causing an electrical discharge. When a neuron is in its rest state, the neuron accumulates and maintains a negative charge within its membrane, thereby polarizing a negative potential (typically −70 mV) between the inside and outside of the neuron. The neuron discharges when a stimulus event increases the membrane potential beyond a certain threshold value (typically −55 mV), thereby triggering an exchange of ions across the neuron's membrane and depolarizing the neuron. The depolarization and exchange of ions causes a positive discharge, also known as a "spike" or "impulse," that peaks at a net positive potential (typically +30 mV). This positive discharge is sent from the neuron through its axon(s) to the dendrites of recipient neurons, which receive, and subsequently respond to, the electrical signal. After the positive discharge, the transmitting neuron returns to its resting state, thereby completing the discharge cycle.

A calcium channel is a structure that spans cell membrane lipid bilayer and allows calcium ions to move passively across the membrane according to the calcium electrochemical gradient between the interior of the cell (where calcium concentration is lower) and the extra-cellular fluid (where calcium concentration is higher). These channels are highly specific to calcium ions, although specificity with respect to other divalent cations is never absolute. Importantly, calcium channels can be activated by changes in the electrical field across the membrane and are therefore said to be "voltage-gated."

Both central and peripheral neurons possess multiple types of voltage-gated calcium channels that often are differentiated on the basis of the membrane potentials at which they are activated. Low-voltage activated calcium current, also called $Ca_v3$-type current, has been observed in a variety of cell types including neurons (White et al. (1989) *Proc. Natl. Acad. Sci.* 86: 6802-6806); Cribbs et al. (2001) *Cir. Res.* 88:403). $Ca_v3$-type current appears to play a key role in the regulation of neuronal bursting and low-amplitude voltage oscillations (Llinas et al. (2006) *J. Neurophysiol.* 95: 3297-3308).

At the macrocellular level, different regions of the brain are responsible for different cognitive and motor functions. Different layers of the cortex control different motor skills as well as distinctive cognitive skills including speech, hearing, sight, touch, smell and thought. The cortex itself has six main cellular levels of neurons (termed levels I-VI) that communicate intracellularly via electrical impulses. Thus, normal cognitive and motor functions are the product of coordinate electrical activity that occurs at the cortical level.

Also at the macrocellular level, the thalamus resides within the center of the brain and acts as a "communications hub" between different regions of the brain, including the cortex. The normal electrical activity of the thalamus is also coordinated, in that the thalamus fires electrical impulses at specific intervals and in a controlled fashion. A complete network of neurons exist between the thalamus and the cortex, thereby creating corticothalamic pathways that facilitate communication and interaction between the thalamus and the cortex.

The thalamus, itself, is divided into regions that include the sensory thalamus and the reticular nucleus. The sensory thalamus is stimulated by signals from other sensory inputs from the body and communicates those inputs to the cortex. The reticular nucleus surrounds the sensory thalamus and acts to suppress the sensory thalamus from transmitting signals at certain times, such as sleep, when the cortex is to be desensitized from communication with the rest of the body. Thus, the reticular nucleus suppresses the electrical activity and discharge of the sensory thalamus.

The thalamus and the cortex are connected through both specific and nonspecific corticothalamic pathways. Specific pathways refer to pathways between the thalamus and particular sensory or motor input regions of the cortex, typically connecting at layer IV of the cortex. Nonspecific pathways refer to pathways between the thalamus and non-sensory and non-motor input regions of the cortex, typically connecting at layers I, IV and/or V of the cortex. Afferent corticothalamic pathways communicate signals from the thalamus to the cortex, whereas efferent corticothalamic pathways communicate signals from the cortex to the thalamus, thereby closing the communication loop between the cortex and the thalamus.

Coordinate electrical activity is characterized by normal neuronal oscillation (i.e., normal frequencies of electrical oscillation by neurons and neuronic regions), wherein neurons and neuronic regions of the brain discharge electrical impulses at particular frequencies, thereby causing electrical oscillation. At the cellular level, inhibitors and neuronal inputs properly control the chemical release of neurons and thereby facilitate normal electrical discharges by the neurons. At the macrocellular level, the interaction and communication between properly discharging neurons causes normal, coordinate electrical activity characterized by electrical oscillation at different frequencies between and among particular regions of the brain.

Neuronal oscillation generally occurs in a plurality of distinct frequency bands. These frequency bands include the theta ($\theta$) band, which includes low frequency oscillations in the 4-8 Hz range that are most commonly associated with the four-phase sleep cycle of human beings. Another significant frequency band is the gamma ($\gamma$) band, which includes high frequency oscillations in the 20-50 Hz range that are associated with sensorimotor and cognitive functions. Individuals experience specific types and amounts of $\theta$ and $\gamma$ band activity based on factors including their mental activity level and physical state. For instance, a person who is asleep will typically experience the four-phase theta-band oscillation cycle associated with sleep, whereas a person who is awake and active will experience gamma-band oscillation at the cortical level to perform cognitive and motor functions.

The present invention relates, in part, to a method of reducing a low-threshold-activated calcium current in a cell by having a $Ca_v3$ plasmalemmal-bound calcium channel. In this method, the extracellular environment of the cell is superfused with a $C_2$-$C_{10}$ alkyl alcohol, or mixtures thereof, in an amount sufficient to modify the voltage-dependent activation kinetics or single channel ionic conductance of the $Ca_v3$ calcium channel such that the low-threshold-activated calcium current in the cell is reduced. As used herein, the term "superfused" refers adding to the fluid that surrounds the tissue.

The term "$C_2$-$C_{10}$ alkyl alcohol" as used herein refers to one or more hydroxyl groups (—OH), attached to a $C_2$-$C_{10}$ alkyl group at any available carbon position. The term "$C_2$-$C_{10}$ alkyl" refers to a linear or branched, saturated hydrocarbon having from 2 to 10 carbon atoms. Representative $C_2$-$C_{10}$ alkyl groups include, but are not limited to, ethyl, propyl, butyl, pentyl, hexyl, heptyl, octyl, nonyl, decanyl, and their respective isomers. Thus, representative $C_2$-$C_{10}$ alkyl alcohols include, but not limited to, ethanol, propanol, butanol, pentanol, hexanol, heptanol, octanol, nonanol, deanol and their respective isomers.

The $C_2$-$C_{10}$ alkyl alcohol can be a straight chain alkyl alcohol such as: $CH_3$—$(CH_2)_n$—OH, wherein n is an integer from 1 to 9, $CH_3$—CH(OH)—$(CH_2)_m$—$CH_3$, wherein m is an integer from 0 to 7; $CH_3$—$CH_2$—CH(OH)—$(CH_2)_p$—$CH_3$, wherein p is an integer from 0 to 6; $CH_3$—$CH_2$—$CH_2$—CH(OH)—$(CH_2)_q$—$CH_3$, wherein q is an integer from 0 to 5; $CH_3$—$CH_2$—$CH_2$—$CH_2$—CH(OH)—$(CH_2)_w$—$CH_3$, wherein w is an integer from 0 to 4; and mixtures of any two or more of the above alkyl alcohols.

Alternatively, the $C_2$-$C_{10}$ alkyl alcohol can be a branched chain alkyl alcohol such as: $(CH_3)_2$CH—$(CH_2)_n$—OH, wherein n is an integer from 0 to 6; $CH_3$—CH(OH)—$(CH_2)_m$—$CH(CH_3)_2$, wherein m is an integer from 0 to 5; $CH_3$—$CH_2$—CH(OH)—$(CH_2)_p$—$CH(CH_3)_2$, wherein p is an integer from 0 to 4; $CH_3$—$CH_2$—$CH_2$—CH(OH)—$(CH_2)_q$—$CH(CH_3)_2$, wherein q is an integer from 0 to 3; $CH_3$—$CH_2$—$CH_2$—$CH_2$—CH(OH)—$(CH_2)_w$—$CH(CH_3)_2$, wherein w is an integer from 0 to 2; and mixtures of any two or more of the above alkyl alcohols.

The $C_2$-$C_{10}$ alkyl alcohol can be a primary, a secondary or a tertiary alcohol. In particular, the $C_2$-$C_{10}$ alkyl alcohol can be 1-octanol or 2-octanol. The $C_2$-$C_{10}$ alkyl alcohol can be present in the extracellular environment at a concentration of from about 10 µM to about 100 µM.

As used herein, "about" means a numeric value having a range of ±10% around the cited value. For example, a range of "about 10 µM to about 100 µM" includes the range "about 9 µM to about 110 µM," the range "about 9 µM to about 90 µM" the range "about 11 µM to about 110 µM," as well as "11 µM to about 90 µM," and all ranges in between.

The cell being treated is a neuron, e.g., an interneuron, a projection thalamic neuron, a reticular thalamic neuron, a cortical interneuron, cortical pyramidal neuron, a basal ganglion neuron, a hippocampus neuron, an amygdala neuron, a tectal neuron, or a cerebellar neuron.

Spike output in neuronal cell types is affected by low-voltage-activated Cav3-type calcium currents arising from $Ca_v3$ channels. There are three isoforms of the Cav3-type calcium channel, i.e., $Ca_v3.1$, $Ca_v3.2$, and $Ca_v3.3$, and they can differ in their voltage-dependent and kinetic properties, showing the potential to differentially affect spike output. In thalamus, differences in the distribution and kinetic properties of Cav3-type currents have been shown capable of influencing the nature of oscillatory output of principal cells and inhibitory interneurons involved in the sleep-wake cycle, suggesting a selective distribution or modulation of $Ca_v3$ channel isoforms over discrete regions of the cell axis. (see, e.g., McKay et al. (2006) *Eur. J. Neurosci.* 24:2581-2594.).

The $C_2$-$C_{10}$ alkyl alcohol can be administered in a pharmaceutically acceptable excipient, carrier, or diluent.

The phrase "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

The present invention also provides a method of inhibiting a $Ca_v3$ plasmalemmal-bound calcium channel in a cell of a mammal in need thereof. The method comprises administering to the mammal a $C_2$-$C_{10}$ alkyl alcohol, or mixtures thereof, at a dose of from about 0.001 mg/kg body weight to about 20 mg/kg body weight of the mammal, for example, from about 0.01 mg/kg body weight to about 1 mg/kg body weight of the mammal, from about 0.1 mg/kg body weight to about 10 mg/kg body weight of the mammal, from about 0.03 mg/kg body weight to about 0.3 mg/kg body weight of the mammal, from about 0.3 mg/kg body weight to about 3.0 mg/kg body weight of the mammal, or about 1.0 mg/kg body weight of the mammal, the alcohol modifying the voltage dependent activation kinetics or single channels ionic conductance of the $Ca_v3$ calcium channel, and thereby inhibiting the $Ca_v3$ calcium channel.

The alcohol can be administered to the mammal orally or parenterally as described below.

In another aspect, the invention provides a method of treating a thalamocortical dysrhythmia disorder in a mammal in need thereof, the method comprising administrating to the mammal a therapeutically effective amount of a $Ca_v3$ calcium channel inhibitor that binds to the $Ca_v3$ calcium channel, thereby reducing a low voltage-activated calcium current in a cell of the mammal.

A thalamocortical dysrhythmia disorder refers to a neurological and/or psychiatric condition arising from the abnormal rhythmicity in particular components of the thalamocortical circuit (Llinás et al. (1999) *Proc. Natl. Acad. Sci. USA*, 96:15222-15227). Thalamocortical dysrhythmia occurs when the coordinate, controlled electrical activity at the cortical level of the brain becomes disrupted, thereby leading to uncoordinated electrical activity and abnormal neuronal oscillation. At the macrocellular level, the abnormal rhythmicity interferes with the communication among and between different regions of the brain, and thereby impairs the motor and cognitive skills that are controlled by those regions of the cortex.

Aspects of the present invention provide a method of treating a neurological disorder in a mammal in need thereof, comprising administering to the mammal a therapeutically effective amount of a pharmaceutical composition as described hereinabove.

Other aspects of the present invention provide a method of treating a thalamocortical dysrhythmia disorder in a mammal in need thereof, comprising administrating to the mammal a therapeutically effective amount of a pharmaceutical composition as described hereinabove.

Non-limiting examples of the neurological disorder associated with thalamocortical dysrhythmia include: Petit Mal Epilepsy (Coulter et al. (1990) *Br. J. Pharmacol.* 100:800-806; Perez-Reyes et al. (2003) *Physiol. Rev.* 83:117-161; Kim et al. (2001) *Neuron,* 31: 35-45; Song et al. (2001) *Soc. Neurosci. Abstr.* 27: 14; Volkmann et al. (1996) *Neurol.,* 46:1359-1370); Parkinson's Disease (Moran et al. (2004) *Soc. Neurosci. Abst.,* 30:676.12; Jeanmonod et al. (1996) *Brain,* 119: 363-375; Llinas et al. (2005) *Trends Neurosci.,* 28:325-333); Tinnitus Llinás et al. (2005) *Trends Neurosci.,* 28:325-333); Jeanmonod et al. (2001) *Thalams & Related Systems* 1:71-79); neurological pain or Central Pain (Schwartzman et al. (2001) *Arch. Neurol.* 58:1547-1550; Schulman et al. (2005) *Thalamus & Related Systems* 3(1): 33-39); Obsessive-Compulsive Disorder (Jeanmonod et al. (2003) *Thalamus & Related Systems* 2:103-113); Tourettes Disease (Moran et al. (2004) *Soc. Neurosci. Abst.* 30:676.12); Chronic Depression (Schulman et al. (2001) *Soc. Neurosci. Abst.* 27); Autism (Sinton et al. (1989) *Plugers Arch.,* 414: 31-36); Schizoaffective Psychosis (Moran et al. (2004) *Soc. Neurosci. Abst.* 30:676.12); Migraine; Absence Epilepsy; and restless legs syndrome, among others.

Aspects of the invention also provide a method of treating a neurological disorder that is not tremor or Parkinson's tremor in a mammal in need thereof. In this method, a therapeutically effective amount of a $Ca_v3$ calcium channel inhibitor is provided to the mammal.

In the therapeutic methods described above, the $Ca_v3$ calcium channel inhibitor is a $C_2$-$C_{10}$ alkyl alcohol, or mixtures thereof. In addition, the $Ca_v3$ calcium channel inhibitor can be a lipophilic molecule with a partition coefficient substantially similar to that of a $C_2$-$C_{10}$ alkyl alcohol. The $Ca_v3$ calcium channel inhibitor can also be a lipophilic molecule with a partition coefficient substantially similar to that of an octanol. In certain cases, the $Ca_v3$ calcium channel inhibitor can be a lipophilic molecule with a molecular weight less than about 160. The lipophilic molecule is a fat soluble molecule that can penetrate a plasmalemmal cell membrane that can interact specifically with the Cav3 type calcium channel. As used herein, "substantially similar" means a value having a range of at least ±5% around the targeted value.

The lipophilic molecule typically has a molecular weight less than about 160. A partition coefficient is a measure of differential solubility of a compound in two solvents. The logarithmic ratio of the concentrations of the solute in the solvent is called log P (sometimes Log P). Typically, the partition coefficient is based on the solvents octanol and water. The octanol-water partition coefficient is a measure of the hydrophobicity and hydrophilicity of a substance. A classical method of log P determination is the shake-flask method, which consists of mixing a known amount of solute in a known volume of octanol and water, then measuring the distribution of the solute in each solvent. The most common method of measuring the distribution of the solute is by UV/VIS spectroscopy. A faster method of log P determination makes use of high-performance liquid chromatography. The log P of a solute can be determined by correlating its retention time with similar compounds with known log P values.

For all of these therapeutic methods, the therapeutically effective amount of the alcohol administered can be from about 0.001 mg/kg body weight to about 20 mg/kg body weight of the mammal, for example, from about 0.01 mg/kg body weight to about 1 mg/kg body weight of the mammal, from about 0.1 mg/kg body weight to about 10 mg/kg body weight of the mammal, from about 0.03 mg/kg body weight to about 0.3 mg/kg body weight of the mammal, from about 0.3 mg/kg body weight to about 3.0 mg/kg body weight of the mammal, or about 1.0 mg/kg body weight of the mammal.

The invention also provides a pharmaceutical composition for treating a neurological disorder in a mammal in need thereof. The composition comprises a therapeutically effective amount of $C_2$-$C_{10}$ alkyl alcohol, or mixtures thereof, and at least one other therapeutic agent. The composition also comprises a therapeutically effective amount of a lipophilic molecule with a partition coefficient substantially similar to that of a $C_2$-$C_{10}$ alkyl alcohol, or mixtures thereof, and at least one other therapeutic agent.

The at least one other therapeutic agent is also administered in an amount effective in reducing the symptoms on the disease or disorder, whether used additively or synergistically in combination with the alcohol. The at least one other therapeutic agent can be administered separately from the pharmaceutical compositions described herein, or it can be administered simultaneously and/or successively with the pharmaceutical compositions described herein.

Effective amounts of the at least one other therapeutic agent are known to those skilled in the art. However, it is within the skilled artisan's purview to determine the at least one other therapeutic agent's optimal effective amount range. In some cases, the patient in need of treatment is being treated with one or more other therapeutic agents. In some other cases, the patient in need of treatment is being treated with at least two other therapeutic agents.

The at least one other therapeutic agent can be, but not limited to, an anticonvulsant or antiepileptic agent, a barbiturate or barbituric acid derivative, an anesthetic agent, a tinnitus-treating agent, a selective serotonin reuptake inhibitor, an antidepressant agent, a neuroleptic agent, an antihypertensive agent, an antipsychotic agent, a calcium channel blocker, an ACE inhibitor, and a beta-blocker.

The anticonvulsant or antiepileptic agent can suppress the rapid and excessive firing of neurons that start a seizure, or can prevent the spread of the seizure within the brain and offer protection against possible excitotoxic effects that may result in brain damage. Many useful anticonvulsant or antiepileptic agents block sodium channels, calcium channels, AMPA receptors, or NMDA receptors. Some useful anticonvulsant or antiepileptic agents inhibit the metabolism of GABA or increase its release.

A useful anticonvulsant or antiepileptic agent includes, but is not limited to, carbamazepine, clobazam, clonazepam, ethosuximide, felbamate, fosphenyloin, flurazepam, gabapentin, lamotrigine, levetiracetam, oxcarbazepine, mephenyloin, phenobarbital, phenyloin, pregabalin, primidone, sodium valproate, tiagabine, topiramate, valproate semisodium, valproic acid, and vigabatrin, diazepam and lorazepam, paraldehyde, and pentobarbital. A useful barbiturate or barbituric acid derivative includes, but is not limited to, sodium thiopental, pentobarbital, secobarbital, amobarbital, butabarbital, barbital, phenobarbital, butalbital, cyclobarbital, allobarbital, methylphenobarbital, secobarbital, vinylbital, and methohexital.

Useful anesthetic agents include, but are not limited to, propofol, etomidate, isoflurane, halothane, and ketamine. A useful tinnitus-treating agent includes, but is not limited to, botulinum toxin, propranolol and clonazepam, zinc supplementation, acamprosate, etidronate or sodium fluoride, lignocaine, carbemazepine, melatonin, sertraline, and vitamin combinations.

Useful selective serotonin reuptake inhibitors include, but are not limited to, paroxetine, sertraline, fluoxetine, and fluvoxamine as well as an antidepressant such as clomipramine. The at least one other active agent may also include gabapentin, lamotrigine, olanzapine and risperidone.

Useful neuroleptic agents include, but are not limited to, risperidone, ziprasidone, haloperidol, pimozide and fluphenazine. Useful antihypertensive agents include, but not limited to, clonidine and guanfacine, atomoxetine (a non-stimulant drug approved for the treatment of attention-deficit hyperactivity disorder). A useful antidepressant agent includes, but is not limited to, clomipramine. A useful atypical antipsychotic agent includes, but is not limited to, clozapine, risperidone, olanzapine, quetiapine, ziprasidone, aripiprazole, and amisulpride, or a typical antipsychotic agent such as chlorpromazine and haloperidol. A useful schizoaffective disorder-treating agent includes, but is not limited to, valproate semisodium or divalproex sodium, Lithium salts, Risperidone, and quetiapine.

The calcium channel blockers are a class of drugs with effects on many excitable cells of the body, like the muscle of the heart, smooth muscles of the vessels or neuron cells. Many calcium channel blockers work by blocking L-type voltage gated calcium channels in the heart, blood vessels, or neuron cells in a brain. This prevents calcium levels from increasing as much in the cells when stimulated, leading to less contraction.

Useful calcium channel blockers include, but are not limited to, amlodipine, felodipine, nicardipine, nifedipine, nimodipine, nisoldipine, nitrendipine, lacidipine, lercanidipine, verapamil, gallopamil, diltiazem, mibefradil, and menthol. The at least one other active agent mentioned above may also include other classes of pharmaceutical agents that have overlapping effects as calcium channel blockers such as ACE inhibitors, beta-blockers, and nitrates. ACE inhibitors include enalapril, ramipril, quinapril, perindopril, lisinopril, benazepril, and fosinopril. Beta-blockers include, but not limited to, dichloroisoprenaline, practolol, pronethaolol, alprenolol, carteolol, levobunolol, mepindolol, metipranolol, nadolol, oxprenolol, penbutolol, pindolol, propranolol, sotalol, timolol, acebutolol atenolol, betaxolol, bisoprolol, esmolol, metoprolol, nebivolol, carvedilol, celiprolol, labetalol, and butoxamine.

The at least one other therapeutic agent mentioned above may alternatively be Parkinson's disorder-treating agent such as, but not limited to, levodopa and its derivatives, carbidopa, benserazide, bromocriptine, pergolide, pramipexole, ropinirole, cabergoline, apomorphine, lisuride, selegiline and rasagiline. These agents are commercially available.

Alternatively, or additionally, the at least one other active agent mentioned above is amiloride (an epithelial sodium channel blocker), α-methyl-α-phenylsuccinimide, pentylenetetrazole, tert-butyl-bicyclo[2.2.2]phosphorothionate. These agents are commercially available.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form will generally be that amount of the compound which produces a therapeutic effect. Generally, out of 100%, this amount will range, for example, from about 1% to about 99% of active ingredient, from about 5% to about 70%, from about 10% to about 30%.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone or in combination with other pharmaceutical agents, or with other anti-thalamocortical dysrhythmia drugs or medicaments, as well as in combination with a pharmaceutically acceptable carrier or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In some cases, these kits are designed for daily administration over the specified term or cycle of administration, in some cases for the number of prescribed administrations per day, and organized so as to indicate a single formulation or combination of formulations to be taken on each day of the regimen or cycle. In some cases, the kit shall have a calendar or days-of-the-week designation directing the administration of the appropriate compositions on the appropriate day or time.

The present invention further provides a method for identifying an alkyl alcohol that modifies the voltage-dependent activation kinetics or single channel ionic conductance of a $Ca_v3$ plasmalemmal-bound calcium channel protein. In this method, atomic coordinates of the $Ca_v3$ calcium channel protein are provided. An alkyl alcohol is then subjected to computational molecular docking. The alcohol that has the optimal virtual binding to the a $Ca_v3$ calcium channel protein is then selected. The optimal virtual binding indicates that the alcohol binds to the a $Ca_v3$ calcium channel protein or alters the properties of the lipid bi-layer at the channel's voltage sensing site.

Computational molecular docking can utilize a computer screening method such as Virtual library screening (VLS) (ICM-VLS, the proposed methodology (software) for this work, represents the state-of-the-art in flexible ligand docking). Optimal virtual binding may be substantially similar to that as shown in FIG. 8.

Computational molecular docking is a research technique for predicting whether one molecule will bind to another, usually a protein. Protein-ligand docking is performed by modelling the interaction between protein and ligand: if the geometry of the pair is complementary and involves favorable biochemical interactions, the ligand will potentially bind the protein in vitro or in vivo. Where the activity of a small molecule ligand (e.g., octanol) is known and desired and the structure of the target protein (e.g., Cav3-type calcium channel) is accessible, computational molecular docking may identify the binding site on the protein, map the pharmacophore space and afford rational improvement of the binding of the said selected ligand to the target protein to eliminate negative biological properties while retaining it therapeutic activity.

In the instant invention, the computational molecular docking of a molecule such as octanol to the Cav3-type calcium channel is specifically addressed to identify optimized ligands to binding a $Ca_v3$ calcium channel and thereby reducing the low-threshold-activated calcium current in a cell. Docking is utilized in the field of drug design (most drugs are small molecules), and using a computational approach allows researchers to quickly screen large databases of potential drugs. Useful docking algorithms for studying the interaction of octanol with Cav3-type calcium channels are flexible ligand docking programs that have performed well in VLS, a procedure whereby thousands of molecules are docked in a short time to the protein in order to detect high-affinity binding agents that may be screened to pharmaceutical activity. See, e.g., Schapira et al., (2000) *Proc. Natl. Acad. Sci. U.S.A*, 97:1008-1013; Schapira et al., (2003) *Proc. Natl. Acad. Sci. U.S.A*, 100:7354-7359); Wang et al., (2003) *Semin. Oncol.*, 30:133-142; Degterev et al., (2001) *Nat. Cell Biol.*, 3:173-182; Gruneberg et al., (2002) *J. Med. Chem.*, 45:3588-3602. ICM-VLS, the proposed methodology (software) for this work, represents the state-of-the-art in flexible ligand docking.

The structure of the Cav3-type calcium channel is not known. However, the crystallographic structure of the related $K_vAP$ and $K_v1.2$ voltage gated K+ channels has been elucidated (Long et al. (2005) *Science*, 309:897-903; Jiang et al. (2003) *Nature*, 423:33-41). ICM docking and VLS has been successfully used to map the pharmacophore space of homology models. Accordingly, homology models of the H and G forms of the Cav3-type calcium channels are constructed and octanol is molecularly docked by computational computer modeling to these homology models. A model of the P-type calcium channel may serve as a negative control.

A three-dimensional model of the complex of octanol with Cav3-type calcium channels emerges from this study. The chemical groups of octanol facing the solvent and not buried in contact with the protein are candidate sites for synthetic alteration to improve the drug-like properties of octanol.

FIG. 8 shows a molecular modeling diagram in one low energy conformation which demonstrates an affinity binding between 1-octanol and a homology model of a subunit of the $Ca_v3$ calcium channel. In further detail, a homology model of a subunit of the $Ca_v3$ calcium channel was constructed, and 1-octanol was docked to it and shown to have a preference for non-specific docking to the lipid phase. One low energy conformation (the one shown in FIG. 8) indicates affinity for the surface between S2 and S5 near the voltage gated S4.

The invention also provides a method of identifying a chemical entity which binds to a $Ca_v3$ calcium channel. In this method, a structure model of the $Ca_v3$ calcium channel is compared with a structure model for the chemical entity. A binding surface on the $Ca_v3$ calcium channel for the chemical entity is then detected.

The invention includes the use of the structural co-ordinates obtainable by subjecting a crystal comprising $Ca_v3$ calcium channel to X-ray diffraction measurements and deducing the structural co-ordinates from the diffraction measurements, to identify, screen, characterize, design or modify a chemical entity. The invention further includes a chemical entity identified by such a method of the invention, wherein the chemical entity reduces the $Ca_v3$ calcium channel-mediated low-threshold-activated calcium current of a $Ca_v3$-channel expressing cell.

The $Ca_v3$ calcium channel is identified as a therapeutic target of alkyl alcohols. The structure of the $Ca_v3$ channel is also identified, and therefore allowing for identification of the amino acid residues involved in binding of alkyl alcohols, such as octanol as well as other inhibitors, to $Ca_v3$ channels.

The identification of the interaction and the structures allows for the characterization or identification of chemical entities which can bind, and in particular, which can reduce $Ca_v3$-mediated low-threshold activated calcium current in a $Ca_v3$ expression to the $Ca_v3$ channel. A number of different types of inhibitors can be identified as discussed in further detail below.

The structure of crystallised $Ca_v3$ channels is envisaged. Typically, the structural coordinates used are obtainable by subjecting a crystal comprising a $Ca_v3$ calcium channel protein, or a fragment thereof, to X-ray diffraction measurements and deducing the structural co-ordinates from the diffraction measurements, to identify, screen, characterize, design or modify a chemical entity. The structural co-ordinates indicate the positions of individual atoms within the crystal and give an indication of the space available for adjusting the position of individual atoms when designing a chemical entity.

The crystal subjected to X-ray diffraction methods comprises a $Ca_v3$ channel protein or a fragment thereof. The $Ca_v3$ protein may be from any source but is most usefully a human $Ca_v3$ protein. The $Ca_v3$ calcium channel may be a modified form. For example, the $Ca_v3$ channel protein may be modified by insertion, deletion, n-terminal or C-terminal addition, or substitution of amino acid by another amino acid. Amino acid substitutions may be conservative substitutions. Typically, when crystallised, a $Ca_v3$ mutant will adopt a similar 3-dimension structure to that adopted by the wild-type channel protein.

References to $Ca_v3$ channel protein herein refer to $Ca_v3$ and homologs thereof. Amino acid residues are defined with reference to the position of the $Ca_v3$ polypeptide. The relevant amino acid residues of homologues of $Ca_v3$ are the equivalent amino acid residues, base on, for example, the best alignment of the homologue to a human or mouse $Ca_v3$.

A $Ca_v3$ polypeptide may be isolated by any suitable means for use in crystallization studies. For example, a $Ca_v3$ polypeptide may be purified using biochemical means from a suitable source. Typically, however, it is convenient to overexpress $Ca_v3$ in cells and purify $Ca_v3$ from those cells. Thus, a polynucleotide encoding a $Ca_v3$ may be used in the construction of a vector. The $Ca_v3$ may be crystallized according to any method known to those skilled in the art. X-ray diffraction may be carried according to any suitable method. The data collected from X-ray diffraction experiments may be processed to deduce the structural co-ordinates of $Ca_v3$ calcium channel using any suitable method.

The invention provides the use of structural co-ordinates to identify, characterize, design or screen a chemical entity. The chemical entity may be one which binds to $Ca_v3$, and/or which acts as an inhibitor of $Ca_v3$-mediated low-threshold activated calcium current a cell. Alternatively, the chemical entity may be a modified $Ca_v3$ polypeptide to alter the activity of the $Ca_v3$ calcium channel.

A chemical entity which binds to or inhibits a $Ca_v3$ calcium channel is any chemical entity capable of forming an association with a $Ca_v3$ polypeptide. The binding or inhibition may be non-specific, for example, such an entity may also bind to or inhibit other calcium channels. More usefully, an agent may be designed or identified which specifically binds to or inhibits the $Ca_v3$ calcium channel. An agent may be designed or identified which is a specific inhibitor of $Ca_v3$, but not other proteins generally or calcium channels in particular.

The structural co-ordinates of $Ca_v3$ allow with skill in the art to predict which amino acids are important in binding an alkyl alcohol and reducing low-threshold activate calcium current. The substrate binding site may be shown as a 2-dimensional representation or a 3-dimensional representation produced by physical models or displayed on a computer screen. Such representations can be used to design, identify or screen chemical entities which bind to or inhibit or are predicted to bind to or inhibit the $Ca_v3$ calcium channel. Such representations can also be used to identify modifications of $Ca_v3$ that alter its activity characteristics.

The representations of the structures may be used in other ways. For example, the representations of the $Ca_v3$ polypeptide may be used to model constraints by the putative introduction of covalent bonds between the atoms which come close together when $Ca_v3$ functions. Representation of the $Ca_v3$ calcium channel may be used to predict which residues of $Ca_v3$ are likely to be involved in steric hindrance. Such residues may be modified, replaced or deleted to decrease esoteric hindrance in order to increase avidity of the peptide for its substrates.

In general, it will be most useful to process the structural co-ordinates obtainable according to the invention in computer-based methods in order to identify or design chemical entities with the desired molecular structure or to identify chemical entities whose structure is complementary to all or part of another chemical entity interest. Thus, chemical entities which are structurally compatible with a $Ca_v3$ polypeptide may be identified or designed.

Such computer-based methods fall into two broad classes: database methods, and de novo designed methods. In database methods, the chemical entity of interest is compared to all chemical entities present in a database of chemical structures and chemical identities whose structure is in some way similar to the compound of interest identified. The structures in the database are based either on experimental data, generated by NMR or X-ray crystallography, or models of 3 dimensional structures based on 2 dimensional data. In de novo design methods, models of chemical entities, for example, such as those which might bind to a $Ca_v3$ target, are generated by a computer program using information derived from known structures and/or theoretical rules.

Similarly, the $Ca_v3$ structural coordinates may be used to screen for the expected activity of chemical entities selected, designed or shown to be modulators such as inhibitors of low-threshold-activated calcium current. For example, the compounds may be screened to assess the likelihood of a $Ca_v3$ binding agent additionally reducing a low-threshold-activated calcium current in a cell. Such screening methods may be useful in identifying agents which selectively reduce $Ca_v3$-mediated low-threshold-activated calcium current, but not other calcium channels generally or other activities of the $Ca_v3$ calcium channel, in particular.

Chemical entities designed or selected according to the methods of the invention may be tested and optimized using computational or experimental evaluation. Experimental methods to assay for the $Ca_v3$-mediated low-threshold-activated calcium current are described in more detail below.

Based on the structure of the $Ca_v3$ polypeptide, a number of different types of inhibitors can be identified.

The following examples illustrate the representative modes of making and practicing the present invention, but are not meant to limit the scope of the invention since alternative methods may be utilized to obtain similar results.

Alternatively, an alteration of the properties of the lipid bi-layer at the channel's voltage sensing site for the chemical entity is detected. Detecting a binding surface or detecting the alteration of the properties of the lipid bi-layer is indicative of the presence of a chemical entity which binds to the $Ca_v3$ calcium channel.

In other aspects, the present invention provides a method of identifying an inhibitor of a $Ca_v3$ calcium channel in a cell. In this method, an isolated $Ca_v3$ plasmalemmal-bound calcium channel is contacted with a candidate compound, and the presence of a complex, or lack thereof, between the $Ca_v3$ calcium channel and the compound is then detected. The candidate compound is an inhibitor if it forms a complex with the $Ca_v3$ calcium channel or alters the properties of the lipid bi-layer at the channel's voltage sensing site. The inhibitor can be any type of molecule or chemical entity that can bind to a $Ca_v3$ channel and stop it from functioning as a $Ca_v3$ calcium channel, e.g., which can reduce $Ca_v3$-mediated low-threshold activated calcium current in a $Ca_v3$ expression to the $Ca_v3$ channel.

The image is oriented with the extracellular mileu at the top and the cytosol at the bottom. The voltage gated paddle containing S4 is at the bottom right. The protein chain is presented as a continuous amino acid sequence with an N- to C-terminus.

Compounds used as pharmaceuticals are usually selective for their intended target or the targets involved in producing the desired effect. A lack of selectivity can lead to toxic side effects that render particular compounds unsuitable for use in human or animal therapy. One approach to identifying compounds that are selective for the intended target is to undertake structural, mechanistic and other analyses on the intended agents and to use the information gained to aid in the preparation of selective compounds, or more selective compounds (relative to those previously known), for use as pharmaceuticals for use in humans or animals. The description describes structural and other studies on the $Ca_v3$ calcium channels that enable the design of selective inhibitors of $Ca_v3.1$, $Ca_v3.2$, and $Ca_v3.3$ on a closely related calcium channels.

The structural model of the $Ca_v3$ calcium channel structural factors or structural coordinates determined by projecting the $Ca_v3$ amino acid sequence onto the structure of a known channel protein.

The invention will be more fully understood by reference to the following examples. They should not, however, be construed as limiting the scope of the invention.

EXAMPLES

Example 1

Preparation of Brain Slices Containing Ventrobasal Thalamic Nucleus

Long-Evans rats (two to four weeks old, 40-50 g; either sex; Taconic Farms) and Harley guinea pigs (four to eight weeks old, 50-300 g) were anesthetized with pentobarbital (Nembutal, 120 mg/Kg i.p.), decapitated and the bone and dura mater covering the cortical surface were carefully peeled away. The rostral part of the brain was glued onto microslicer stage of a vibroslicer (Leica Microsistemas, Bannockburn, Ill., USA) containing a low $Na^+$/high sucrose artificial cerebrospinal fluid ("ACSF") solution (248 mM sucrose, 26 mM $NaHCO_3$, 1.25 mM $NaH_2PO_4$, 5 mM KCl, 3 mM $MgSO_4$, 0.5 mM $CaCl_2$, 10 mM (+)-sodium-L-ascorbate, 3 mM sodium pyruvate and 10 mM glucose, aerated with 95% $O_2$/5% $CO_2$ to a final pH of 7.4). 180 µm to 240 µm transverse slices were obtained containing both thalamic and cortical areas. After cut, slices were allowed to recover in an incubation chamber at 37° C. for at least 30 min. containing continuously oxygenated combination of half-half low $Na^+$/high sucrose-normal ACSF (124 mM NaCl, 5 mM KCl, 1.25 mM $KH_2PO_4$, 26 mM $NaHCO_3$, 1.2 mM $MgCl_2$, 2.4 mM $CaCl_2$, and 10 mM glucose, pH 7.4).

Example 2

Whole-Cell Patch Recording Methods

Patch recordings were performed at 35° C. in a chamber constantly perfused with normal ACSF solution containing carbachol (50 µM-100 µM, a cholinergic agonist, both nicotinic and muscarinic), tetrodotoxin (100 nM-500 nM, a voltage-dependent sodium channel blocker) and an equivalent proportion of the vehicle Tween-80 used to dissolve octanol Winds et al. (1982) *Nature* 297:406-408.). Patch electrodes were made from borosilicate glass and had resistances of 3 to 8 MΩ when filled with either high potassium intracellular solution (130 mM $KMeSO_3$, 10 mM NaCl, 10 mM HEPES, 1 mM EGTA, 4 mM Mg-ATP, 0.4 mM Na-GTP, 2 mM $MgCl_2$, 10 mM sucrose and 10 mM phosphocreatine, pH 7.3, 290 mOsm); or either a high cesium/QX314 intracellular solution (120 mM $CsMeSO_3$, 8 mM NaCl, 10 mM HEPES, 5 mM EGTA, 10 mM TEA-Cl (triethylamine chloride), 4 mM Mg-ATP, 0.5 mM GTP, 7 mM phosphocreatine, pH 7.3 (29 mOsm)). High potassium solution was used when octanol-dependent effects were studied on both basic membrane properties as well as on the pattern of action potentials of thalamic neurons. High Cs/QX314 was used to quantify the blocking effect of octanol on the voltage-sensitive calcium currents.

Neurons were recorded using an Axopatch 700B amplifier (Axon Instruments, Molecular Devices, Sunnyvale, Calif., USA) in combination with the PCLAMP 10.0 software (Axon Instruments, Molecular Devices, Sunnyvale, Calif., USA). Data were filtered at 5 kHz, digitalized, and stored on a computer to further analysis off-line. Access resistance (8-20MΩ) was continuously monitored during experiments.

Example 3

A. Inhibition of $Ca_v3$ Plasmalemmal-Bound Calcium Channel with 1-Octanol

Figure 1A:
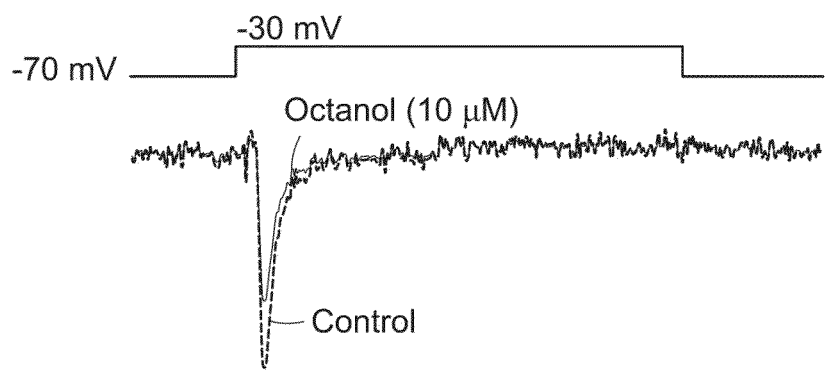
FIG. 1A is a schematic representation of recording from an experiment showing the effect of 1-octanol on $Ca_v3$ calcium current at different voltage levels using a voltage clamp technique.
Figure 1B:
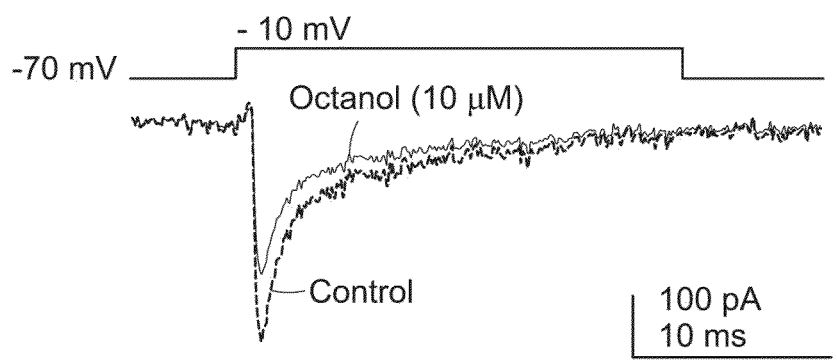
FIG. 1B is a schematic representation of recording showing the effect of 1-octanol on the peak of the fast component (T-currents) but not the slow component when both low and high voltage activated calcium currents are open in a cell.

FIGS. 1A and 1B show the patch recording of individual thalamic neurons from the ventrobasal nucleus obtained from the rodents' brain slices prepared according to Example 1. The thalamic nucleus processes the somatosensory information from rodents' whiskers. The effect of 10 µM octanol on calcium channels at two different voltage levels was shown.

Using a holding level where only low voltage activated calcium currents can be open (−30 mV), octanol blocks peak fast activated $Ca_v3.1$ calcium current (ICa) amplitude by about 30% (FIG. 1A). When both low and high voltage activated calcium currents are open, octanol blocks the peak of the fast component ($Ca_v3.1$) leaving unchanged the slow component that remains open at the end of the depolarized pulse (−10 mV)(FIG. 1B). Therefore, 1-octanol is shown to specifically block low threshold activated Cav3-type currents from Ventrobasal thalamic neurons.

B. Inhibition of $Ca_v3$ Plasmalemmal-Bound Calcium Channel with 2-Octanol

FIGS. 2A and 2B show the blocking effect of clinical concentrations of 2-octanol directly on the low threshold activated calcium currents using a high Cs/QX314 intracellular solution in a voltage-clamp mode, as described in EXAMPLE 2.

When a concentration of 100 µM 2-octanol is applied, the low threshold activated $Ca_v3$ calcium currents are completely abolished. FIG. 2A shows four representative $Ca_v3$ calcium current activated after depolarizing the thalamic neuron from a holding potential of −70 mV to −60 mV, −30 mV, −20 mV and −10 mV using square pulses (FIG. 2A, top). In this case, a progressive reduction of the $Ca_v3$ calcium currents peak is observed for increasing 2-octanol concentrations. FIG. 2B shows the current-voltage (i.e., I-V curve) relationship for the same thalamic neuron described in FIG. 2A, but for a wider range of holding potentials. Similarly, $Ca_v3$ peak currents are partially reduced at 10 µM 2-octanol while almost abolished at 100 µM 2-octranol.

C. Inhibition of Thalamic Low Frequency Oscillations with 2-Octanol

FIGS. 3A and 3B show the effect of clinical levels of 2-octanol on thalamic cell intrinsic oscillatory activity using intracellular recording from thalamic cells in vitro.

Octanol selectively blocks thalamic low frequency oscillations. This finding is in keeping with the results illustrated in FIGS. 1 and 2, as such oscillations are mediated by low threshold activated calcium conductance (Jahnsen et al., *J. Physiol.* (London) 346:205-226). FIG. 3A (black lines) shows a pair of low threshold spikes firing at 2 Hz generated after the rebound of a short hyperpolarizing pulse is applied (FIG. 3 B). Once the activation paradigm is established, five min. of perfusion with 10 µM 2-octanol results in a complete abolishment of the oscillatory activity, which is partially reversible after 40 min. of washout to remove the 2-octanol.

D. Inhibition of $Ca_v3$ Plasmalemmal-Bound Calcium Channel with 1-Octanol

FIGS. 4A and 4B are traces showing the effect of 1-octanol on low-threshold calcium spikes using a current clamp technique, as described in EXAMPLE 2.

The results show that the effect of 1-octanol on the low threshold spikes is concentration-dependent. The application of 1-octanol increments membrane resistance (i.e., a greater change in membrane potential after the injection of the same amplitude current pulse) after blocking Cav3 calcium currents (as shown in FIGS. 1 and 2). FIGS. 4A and 4B also show that 1-octanol at the concentration of 50 µM (dotted lines) further decreases the peak of low threshold spikes activated using ramps of current instead of square pulses.

E. Activation of Low Threshold Spikes in Thalamic Neurons

FIGS. 5A and 5B demonstrate that low threshold spikes can be activated following TTX removal from the external solution using a current clamp technique. After TTX removal from the external normal ACSF solution (as described in EXAMPLE 2), low threshold spikes can be activated in the presence of fast action potential mediated by voltage-sensitive sodium channels. In control conditions and after a long hyperpolarizing pulse, thalamic neurons respond with a low threshold spike on top of which several action potentials can be observed (FIGS. 5A and 5B). Under these conditions, after 2-octanol's block of low threshold spike, the increment in input resistance notably increased the frequency of action potentials of the thalamic neurons (FIGS. 5A and 5B).

F. Inhibition of Thalamic High-Frequency Subthreshold Oscillations with 1-Octanol With TTX Comparison With TTX Plus 1-Octanol The effect of (1) tetrodotoxin ("TTX") and (2) TTX and 1-octanol on the high-frequency subthreshold oscillation previously described in the Ventrobasal thalamic neurons (Pedroarena & Llinas (1997) Proc. Natl. Acad. Sci. USA. 94(2): 724-728) was tested. Using patch configuration and high-$K^+$ intracellular solution, in the presence of TTX (2 µM), thalamic neurons from wild-type mouse respond with a low threshold spike after hyperpolarizing square pulses (FIG. 6A, wildtype, up left black lines) while depolarizing square pulses result in a clear 40 Hz oscillation (FIG. 6A, wildtype, up left, inset). Following the application of 50 µM octanol, 40 Hz oscillations are observed while the rebound low threshold spike is abolished (FIG. 6, wildtype, up right, inset, red lines). When the alpha-1A subunit of the P/Q-type calcium channels is absent due to a homozygous knock-out mutation (FIG. 6, alpha1A-KO), a clear low threshold spike is present in the thalamic neurons (also blocked by octanol, see FIG. 6B, alpha1A-KO, bottom right) while no high-frequency 40 Hz oscillations are present (FIGS. 6A and 6B, alpha1A-KO, bottom left and right insets) either before or after octanol application.

The examples show that applications of clinical concentrations of octanol at micromolar level administration result in a reversible membrane conductance modification that can significantly reversibly block the low threshold activated $Ca_v3$ calcium currents of the neurons present in the thalamic Ventrobasal nucleus. These results in an electrical activation change where thalamic neurons fail to generate low frequencies, either spontaneously or by being evoked. This effect is further demonstrated by increasing the concentration of octanol to 50 mM and determining the resulting effects on the low threshold spikes generated by a slow change in membrane potential using a ramp of current in the presence of TTX.

This selective block of $Ca_v3$ calcium currents allows continued activity of these neurons at higher frequencies. Indeed, octanol does not appear to affect the high frequency oscillations in the thalamic neurons. Accordingly, the specific repression of low frequency oscillations with octanol provides an appropriate pharmacological tool to reduce the low frequency oscillations observed in patients with thalamocortical dysrhythmias while leaving untouched the mechanisms by which high-frequency oscillations are generated in the thalamocortical system.

Example 4

The Effect of Octanol on Frequency Profiles Presented in Wild Type and alpha-1A Knockout Mice Alpha1A knockout mice, which have an enhanced Cav3 calcium channel activity, develop progressive neurological symptoms resembling Thalamo-cortical Dysrhythmia characterized specifically by ataxia and dystonia, before dying, around four weeks after birth (Jun et al. (1999) Proc. Natl. Acad. Sci. USA. 96(26):15245-50).

FIG. 7A shows an EEG recording during 30 seconds from a wild type mouse where a characteristic low amplitude EEG recording can be observed. When a Fast Fourier transform analysis is performed in two segments of 1 second each (FIG. 7A, segments a and b) from the same wild type trace, a wide range of frequencies is observed. Importantly, the presence of high frequencies in the range of gamma band is observed (FIG. 7A, red arrows). In contrast, an alpha-1A knockout mouse presents a totally different EEG recoding. As shown in FIG. 7B, the presence of high amplitude low frequency is characteristic. Furthermore, the frequency analysis of these alpha-1A animals shows no high frequencies presented when one-second interval is used (FIG. 7B, segments c and d).

As in the FIG. 7C the wild type (another way to say control) and the mutant mouse recordings are compared. The increase activity produced by the increase of Cav3 channel results in a large increase in low frequencies (Thalamo-cortical Dysrhythmia [TCD]). A more detail plot of frequencies show that the lower frequencies (theta 2-8 Hz) are increased and the higher frequencies are absent (red bars in the plot) while the control displays the normal 10 Hz (alpha rhythm) and 40 Hz (gamma rhythm). It is expected that Octanol given to the mutant mice will reduce the amplitude of the theta rhythm, demonstrating is use as a possible TCD pharmaceutical compound.

The administration of 1-octanol (Sinton et al., (1989) Pflügers Archiv 414: 31-36) in wild types versus knockout mice allows the quantification of the effects of such a drug in the high and low frequencies in the EEG. Since knockout mice only present low frequencies, a dose-response curve of 1-octanol can be easily prepared. Also, an augmentation in the ratio of high/low frequencies is expected for the wild types treated with 1-octanol.

As shown in FIG. 7D, following octanol administration (i.p., 0.2 mg/kg) the second line of EEG activity and a faster sweep inset. Analysis of the frequency components plotted in blue bars show a decrease in the low frequencies (0-15 Hz) and an increase in hi frequencies (30-45 Hz) consistent with the fact that Cav3 channels are responsible for low frequencies and their block produces an increase in high frequency.

Example 5

Methods for Identifying an Alkyl Alcohol that Binds to a $Ca_v3$ Plasmalemmal-Bound Calcium Channel Using Computational Molecular Docking A homology model of a single subunit of the $Ca_v3$ calcium channel is made as described above, and 1-Octanol is docked to it using computational methods. The results in FIG. 8 show a preference for non-specific docking to the lipid phase. One low energy conformation indicates affinity for the surface between S2 and S5 near the voltage gated S4.

The image is oriented with the extracellular milieu at the top and the cytosol at the bottom. The voltage gated paddle containing S4 is in white at the bottom right. The protein chain is colored in a gradient from N- to C-terminus with dark blue being the N-terminus and dark red being the C-terminus. FIG. 8 shows an image of the model of the tetramer of the $Ca_v3$ calcium channel. The yellow balls at the bottom are the location of the ion channel and correspondingly the domain in which they are located is the transmembrane domain of the channel. The low energy conformation of octanol is shown in green near the channel in the voltage gate area of the tetramer.

EQUIVALENTS

All numbers expressing quantities of ingredients, reaction conditions, analytical results and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

We claim:
1. A method of treating a thalamocortical dysrhythmia disorder in a mammal in need thereof, the disorder resulting from abnormal hyperpolarization of a thalamic neuron having a protractedly activated $Ca_v3$ channel and an increased low threshold calcium current, the disorder being Migraine, restless leg syndrome, obsessive compulsive disorder, Tourette's disorder, autism, or Asperger's syndrome, and not tremor or Parkinson's tremor,
the method comprising inhibiting the $Ca_v3$ calcium channel by administering to the mammal an inhibitor which binds to the $Ca_v3$ calcium channel, thereby reducing the low threshold calcium current in and hyperpolarization of the neuron,
wherein the $Ca_v3$ calcium channel inhibitor is a $C_2$-$C_{10}$ alkyl alcohol, a lipophilic molecule with a partition coefficient at least 5% that of a $C_2$-$C_{10}$ alkyl alcohol, or mixtures thereof.

2. The method of claim 1, wherein the inhibitor is a lipophilic molecule with a partition coefficient ranging from at least 5% that of an octanol.

3. The method of claim 1, wherein the inhibitor is a lipophilic molecule with a molecular weight less than about 160.

4. The method of claim 1, wherein the $C_2$-$C_{10}$ alkyl alcohol is administered in a pharmaceutically acceptable excipient, carrier, or diluent.

5. The method of claim 1, wherein the therapeutically effective amount administered is from about 0.001 mg/kg body weight to about 20 mg/kg body weight of the mammal.

6. The method of claim 1, wherein the therapeutically effective amount administered is from about 0.1 mg/kg body weight to about 10 mg/kg body weight of the mammal.

7. The method of claim 6, wherein the therapeutically effective amount administered is from about 0.3 mg/kg body weight to about 3.0 mg/kg body weight of the mammal.

8. The method of claim 6, wherein the therapeutically effective amount administered is about 1.0 mg/kg body weight of the mammal.

9. The method of claim 1, wherein the alcohol is administered orally.

10. The method of claim 1, wherein the alcohol is administered parenterally.

11. The method claim 1, wherein the $C_2$-$C_{10}$ alkyl alcohol is selected from the group consisting of:
(a) $CH_3$—$(CH_2)$n-OH, wherein n is an integer from 1 to 9;
(h) $CH_3$—$CH(OH)$—$(CH_2)$m-$CH_3$, wherein m is an integer from 0 to 7;
(c) $CH_3$—$CH_2$—$CH(OH)$—$(CH_2)$p-CH, wherein p is an integer from 0 to 6;
(d) $CH_3$—$CH_2$—$CH_2$—$CH(OH)$—$(CH_2)$q-$CH_3$, wherein 1 is an integer from 0 to 5;
(e) $CH_3$—$CH_2$—$CH_2$—$CH_2$—$CH(OH)$—$(CH_2)$w-$CH_3$, wherein w is an integer from 0 to 4; and
(f) mixtures thereof.

12. The method of claim 1, wherein the $C_2$-$C_{10}$ alkyl alcohol is 1-octanol.

13. The method of claim 1, wherein the $C_2$-$C_{10}$ alky alcohol is 2-octanol.

14. A method of treating a thalamocortical dysrhythmia disorder in a mammal in need thereof, the disorder resulting from abnormal hyperpolarization of a thalamic neuron having a protractedly activated $Ca_v3$ channel and an increased low threshold calcium current, the disorder being Migraine, restless leg syndrome, obsessive compulsive disorder, Tourette's disorder, autism or Asperger's syndrome, and not tremor or Parkinson's tremor, the method comprising inhibiting the $Ca_v3$ calcium channel in the neuron by administering to the mammal a therapeutically effective amount of a pharmaceutical composition comprising:

an inhibitor which binds to the $Ca_v3$ calcium channel, thereby reducing the low threshold calcium current in and hyperpolarization of the neuron, the inhibitor being a $C_2$-$C_{10}$ alkyl alcohol, a lipophilic molecule with a partition coefficient at least 5% that of a $C_2$-$C_{10}$ alkyl alcohol, or mixtures thereof; and at least one other therapeutic agent selected from the group consisting of: a barbiturate or barbituric acid derivative, an anesthetic agent, a selective serotonin reuptake inhibitor, an antidepressant agent, a neuroleptic, an antihypertensive agent, an antipsychotic agent, a calcium channel blocker, an ACE inhibitor, or a beta blocker.

15. The method of claim 14, wherein the inhibitor is 1-octanol, 2-octanol or mixtures thereof.

\* \* \* \* \*

UNITED STATES PATENT AND TRADEMARK OFFICE
CERTIFICATE OF CORRECTION

| | |
|---|---|
| PATENT NO. | : 8,614,254 B2 |
| APPLICATION NO. | : 12/843108 |
| DATED | : December 24, 2013 |
| INVENTOR(S) | : Llinas et al. |

It is certified that error appears in the above-identified patent and that said Letters Patent is hereby corrected as shown below:

In the Claims

Claim 11(c), beginning at Column 26, Line 52, should read as follows:

(c) $CH_3\text{-}CH_2\text{-}CH(OH)\text{-}(CH_2)p\text{-}CH_3$, wherein p is an integer from 0 to 6;

Signed and Sealed this
Fourth Day of March, 2014

Michelle K. Lee
*Deputy Director of the United States Patent and Trademark Office*